(12) United States Patent
Sauer

(10) Patent No.: US 10,835,220 B2
(45) Date of Patent: Nov. 17, 2020

(54) SELF-ARTICULATING JOINT FOR A MINIMALLY INVASIVE SURGICAL APPARATUS

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 210 days.

(21) Appl. No.: 16/132,217

(22) Filed: Sep. 14, 2018

(65) Prior Publication Data

US 2019/0008497 A1 Jan. 10, 2019

Related U.S. Application Data

(63) Continuation of application No. 14/248,798, filed on Apr. 9, 2014, now Pat. No. 10,105,126.

(51) Int. Cl.
*A61B 17/00* (2006.01)
*A61B 17/32* (2006.01)
*A61B 17/29* (2006.01)
*A61B 17/34* (2006.01)

(52) U.S. Cl.
CPC ........ *A61B 17/00234* (2013.01); *A61B 17/29* (2013.01); *A61B 17/320016* (2013.01); *A61B 17/3421* (2013.01); *A61B 2017/00738* (2013.01); *A61B 2017/2901* (2013.01); *A61B 2017/2908* (2013.01); *A61B 2017/2927* (2013.01)

(58) Field of Classification Search
CPC .......... A61B 17/00234; A61B 17/0483; A61B 17/22031; A61B 17/28; A61B 17/2812; A61B 17/2816; A61B 17/282; A61B 17/2833; A61B 17/2841; A61B 17/29; A61B 17/2909; A61B 17/30; A61B 17/32; A61B 17/320016; A61B 17/320092; A61B 17/3421; A61B 17/42; A61B 2017/0069; A61B 2017/00738; A61B 2017/2837; A61B 2017/2845; A61B 2017/2901; A61B 2017/2905; A61B 2017/2908; A61B 2017/291; A61B 2017/2919; A61B 2017/2926; A61B 2017/2927; A61B 2017/2929; A61B 2017/2931; A61B 34/30; A61B 34/32; A61B 2034/305; A61B 2034/306; B25B 7/00; B25B 7/06; B25B 7/10
See application file for complete search history.

(56) References Cited

U.S. PATENT DOCUMENTS

| | | |
|---|---|---|
| 5,201,739 A | 4/1993 | Semm |
| 5,304,185 A | 4/1994 | Taylor |
| 5,431,666 A | 7/1995 | Sauer |
| 5,562,686 A | 10/1996 | Sauer |
| 5,766,183 A | 6/1998 | Sauer |

(Continued)

*Primary Examiner* — Wade Miles
*Assistant Examiner* — Kankindi Rwego
(74) *Attorney, Agent, or Firm* — David J. Gervasi; Christopher B. Miller

(57) ABSTRACT

A self-articulating joint is disclosed for a minimally invasive surgical apparatus. The self-articulating joint has a first elbow component pivotably coupled to a second elbow component, wherein the first and second elbow components are biased to form a non-linear angle relative to each other. The self-articulating joint also has an elbow latch configured to releasably hold the first and second elbow components at a substantially fixed non-linear operating angle.

5 Claims, 22 Drawing Sheets

(56) References Cited

U.S. PATENT DOCUMENTS

| | | |
|---|---|---|
| 6,368,334 B1 | 4/2002 | Sauer |
| 6,533,796 B1 | 3/2003 | Sauer |
| 6,641,592 B1 | 11/2003 | Sauer |
| 6,997,931 B2 | 2/2006 | Sauer |
| 7,211,093 B2 | 5/2007 | Sauer |
| 7,407,505 B2 | 8/2008 | Sauer |
| 7,481,824 B2 | 1/2009 | Boudreaux |
| 7,731,727 B2 | 6/2010 | Sauer |
| 8,313,496 B2 | 11/2012 | Sauer |
| 8,353,898 B2 | 1/2013 | Lutze |
| 8,398,657 B2 | 3/2013 | Sauer |
| 8,562,592 B2 | 10/2013 | Conlon |
| 8,568,390 B2 | 10/2013 | Mueller |
| 8,584,921 B2 | 11/2013 | Scirica |
| 8,652,149 B2 | 2/2014 | Sauer |
| 2009/0171159 A1 | 7/2009 | Jorgensen |
| 2009/0222027 A1 | 9/2009 | Sauer |
| 2012/0016383 A1 | 1/2012 | Sauer |
| 2012/0286020 A1 | 11/2012 | Smith |
| 2013/0158569 A1 | 6/2013 | Chu |
| 2013/0270322 A1 | 10/2013 | Scheib |
| 2013/0297013 A1 | 11/2013 | Klima |
| 2013/0304083 A1 | 11/2013 | Kaercher |
| 2014/0012255 A1 | 1/2014 | Smith |

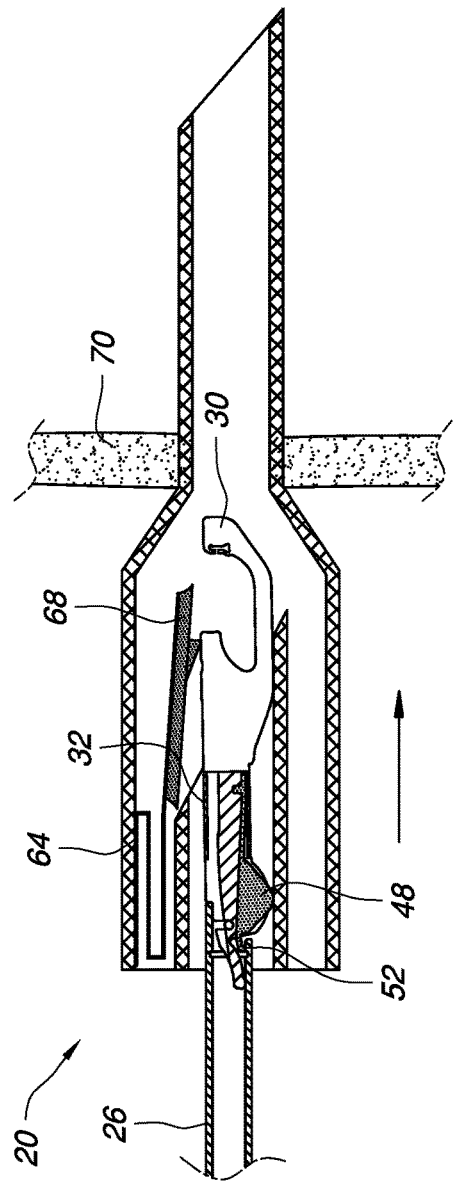
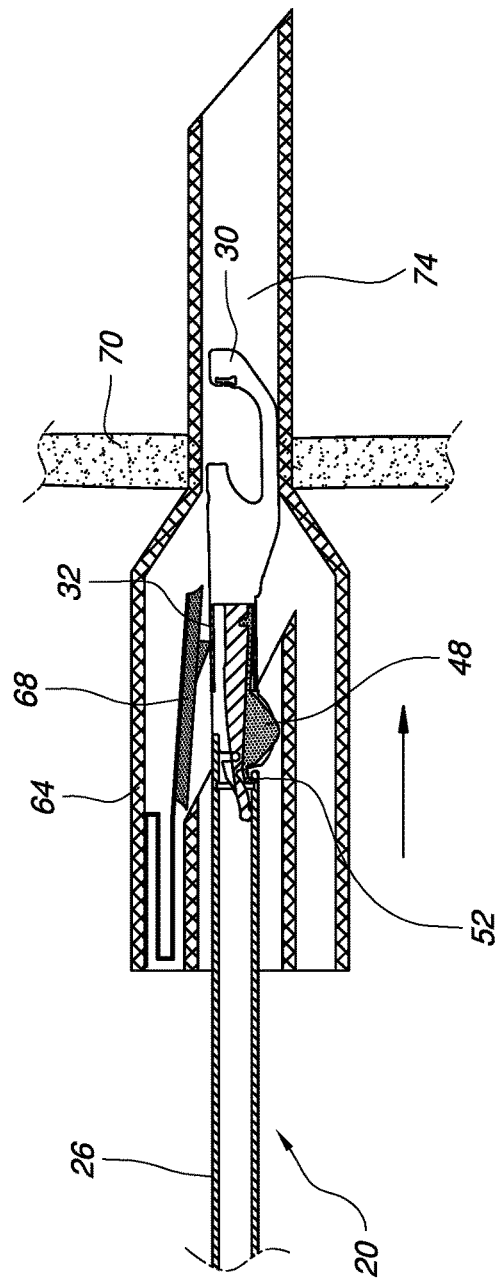

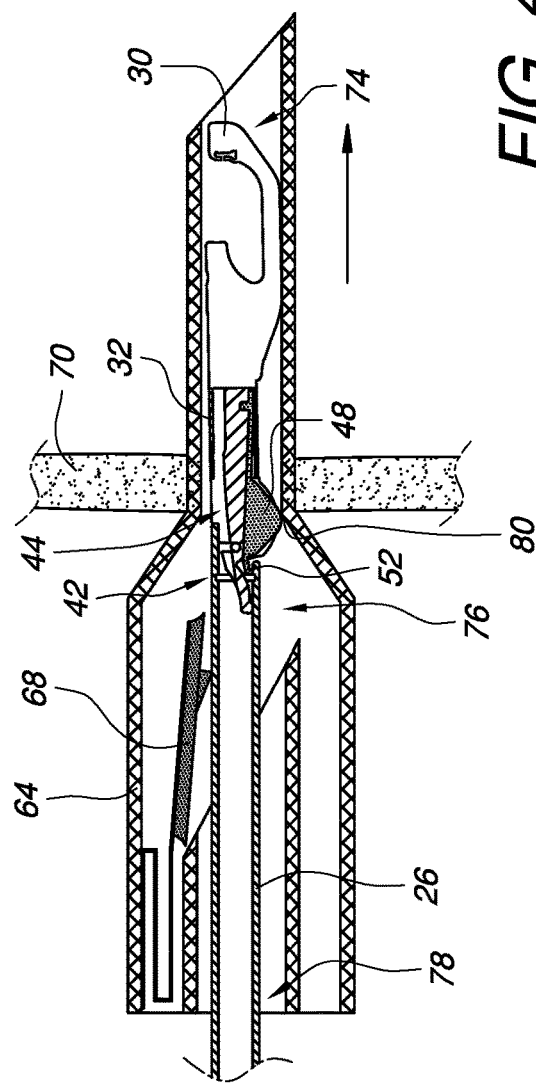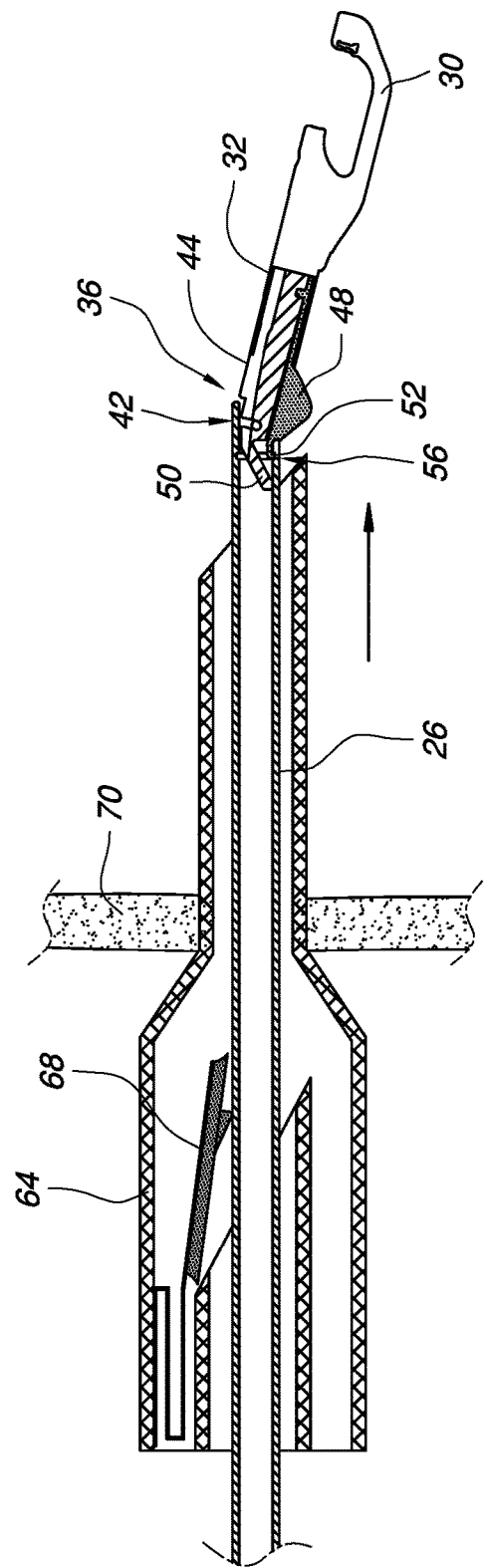

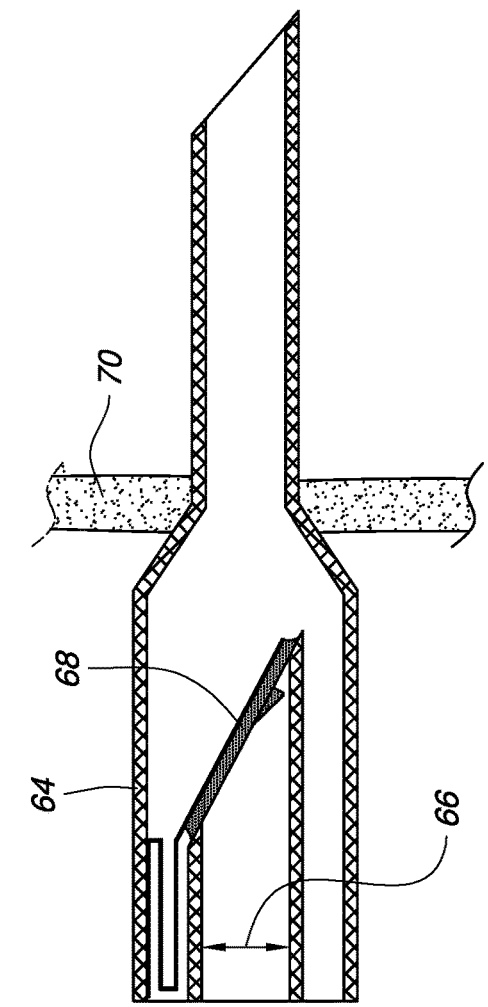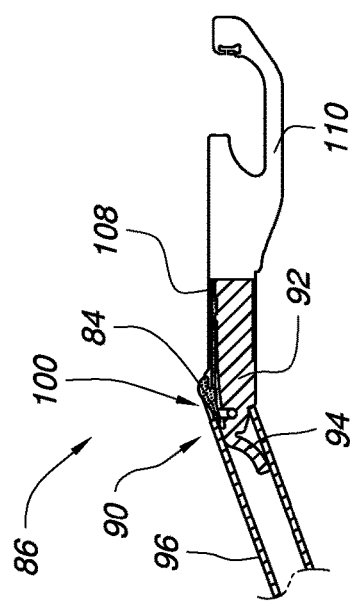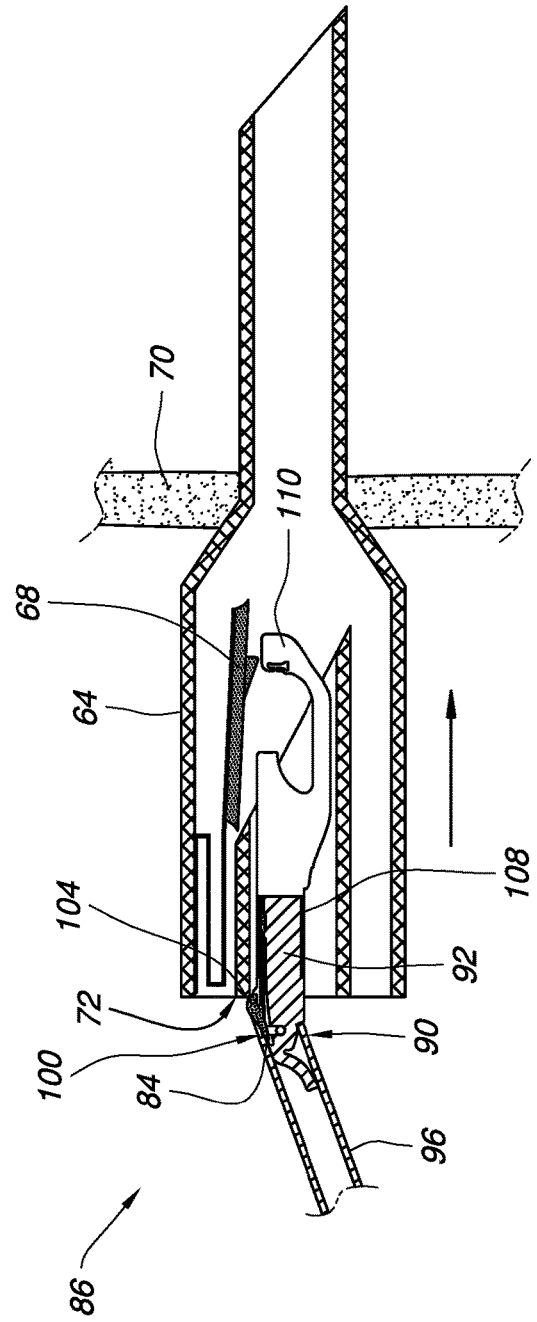
FIG. 7A
FIG. 7B

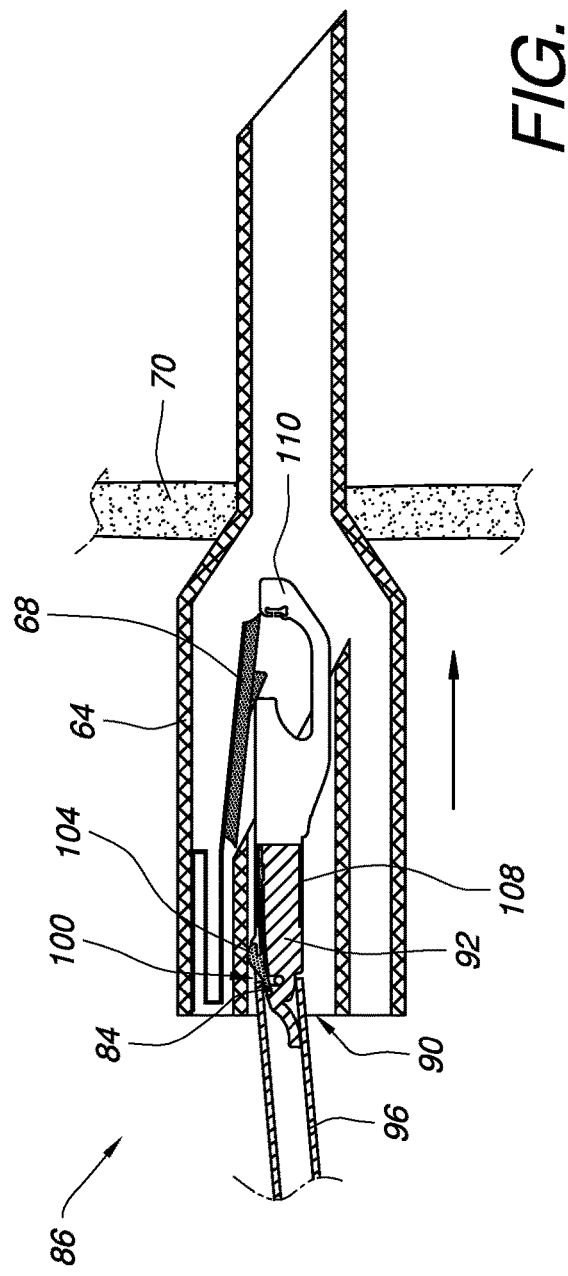
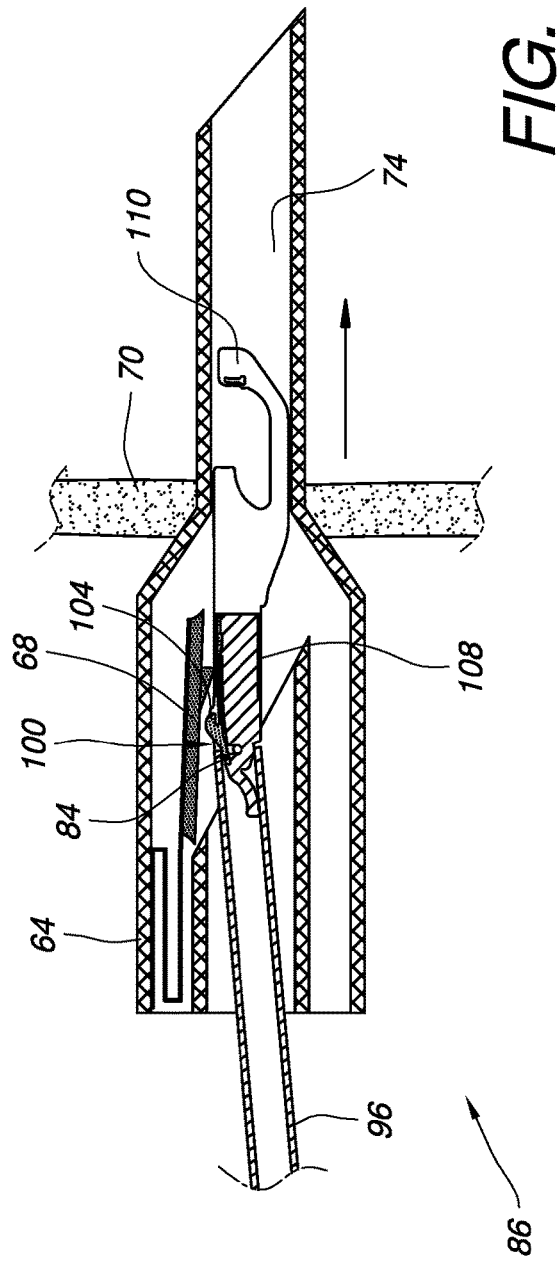

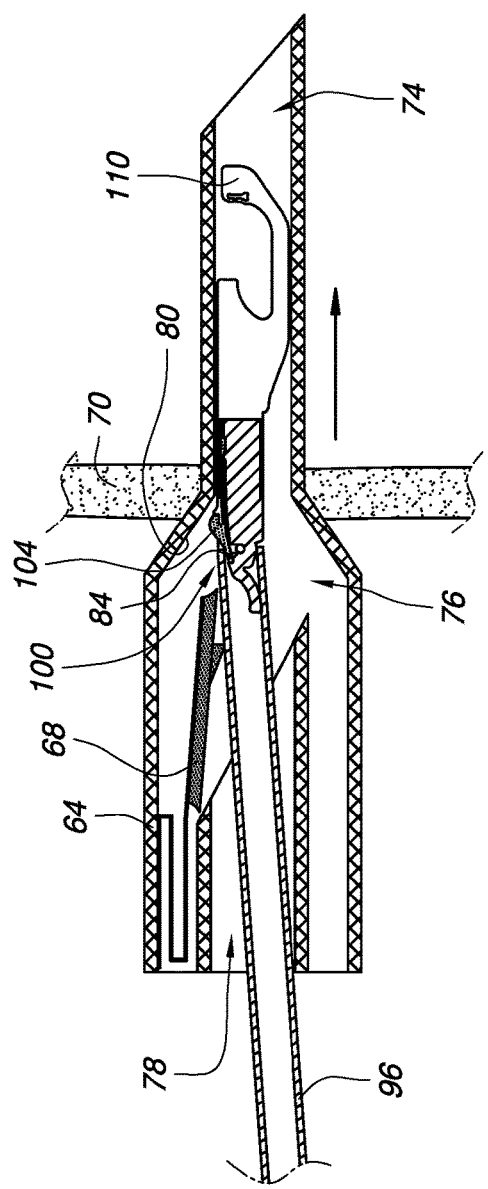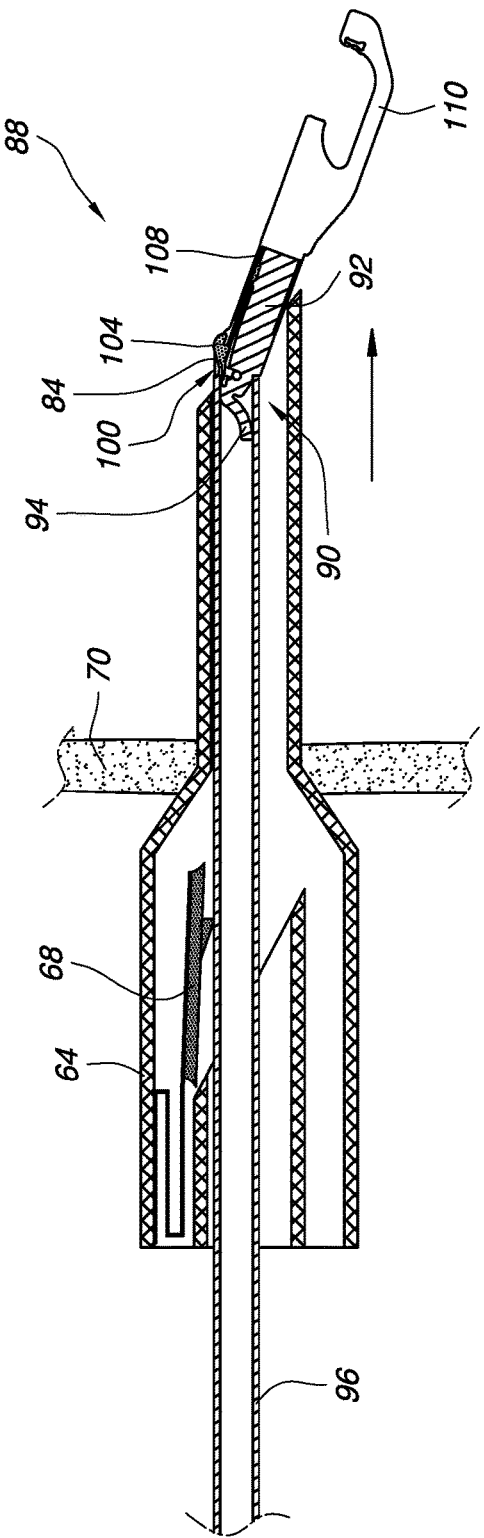

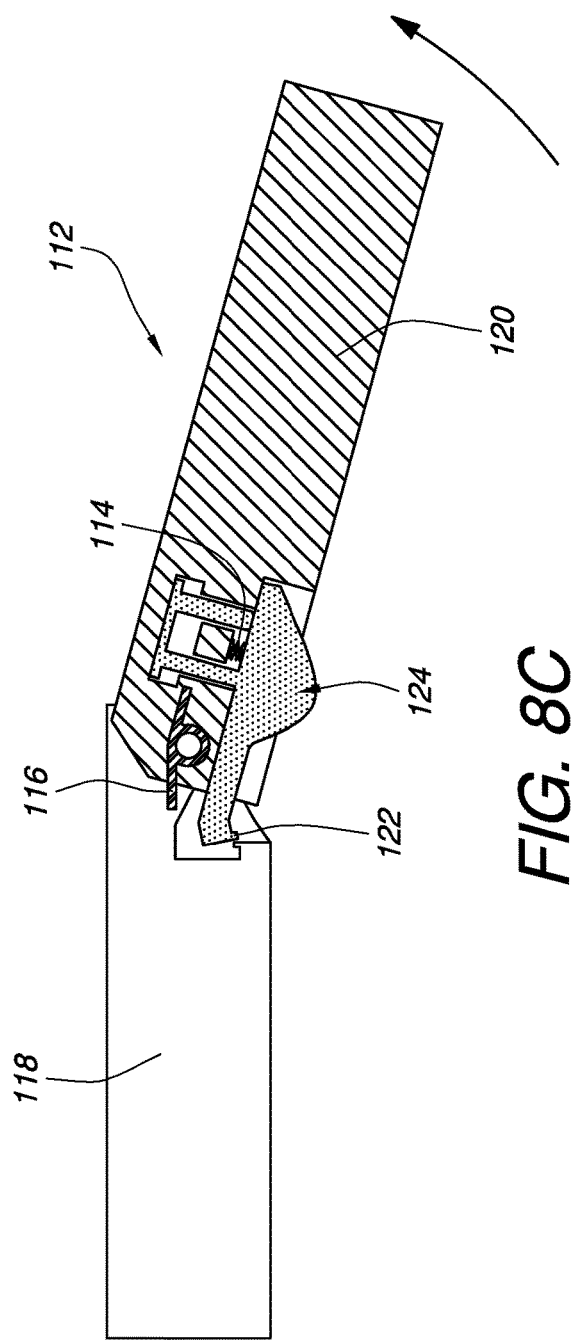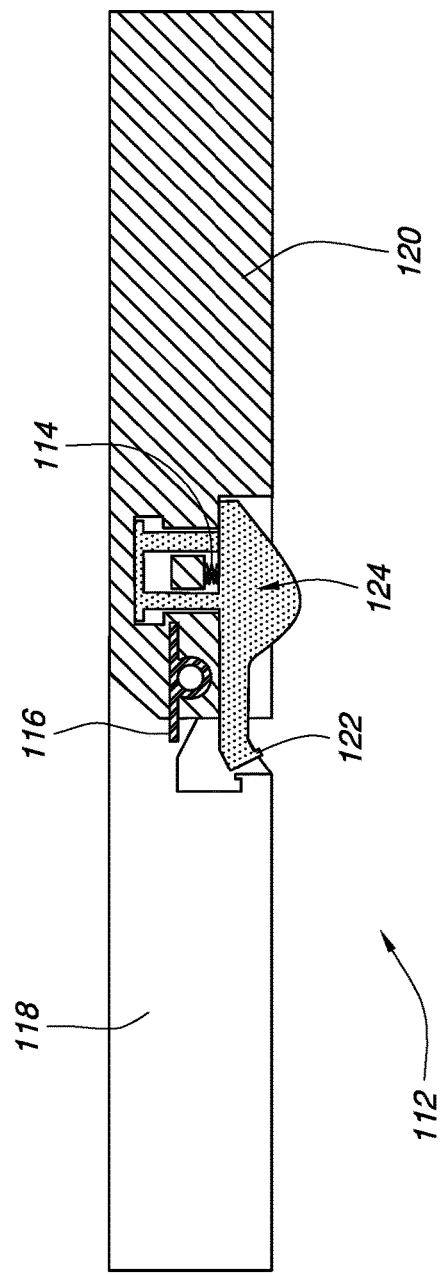

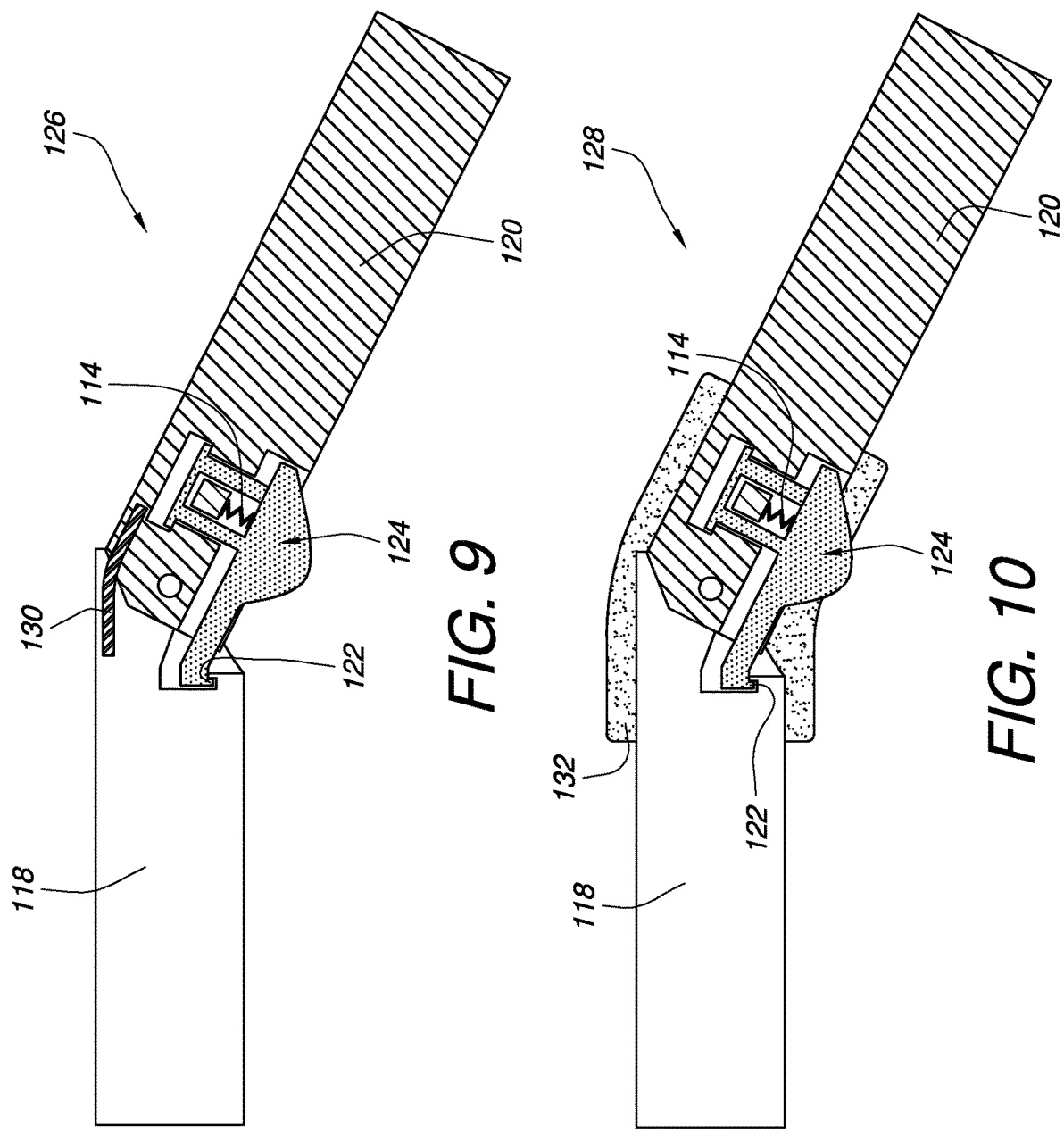

SELF-ARTICULATING JOINT FOR A MINIMALLY INVASIVE SURGICAL APPARATUS

FIELD

The claimed invention relates to surgical apparatuses and, more specifically, to a self-articulating joint for use in a minimally invasive surgical apparatus.

BACKGROUND

Minimally invasive surgery (MIS) has allowed physicians to carry out many surgical procedures with less pain and disability than conventional, open surgery. However, unlike conventional open surgery, where the surgical site is readily accessible through a large incision, MIS typically requires the surgeon to operate remotely by inserting and manipulating instruments through small punctures, openings, or access sites in the body wall. A hollow cannula may be placed in the puncture to create a minimally invasive entry point. Cannulas, typically have tubular passages with a diameter ranging in size from 5 to 20 millimeters (mm) and are often sealed to maintain positive pressure within the peritoneal cavity to facilitate pneumoperitoneum during laparoscopic surgery. One or more cannulas may be inserted into the body for any given operation. Medical instruments, such as grippers, manipulators, cutters, suturing (sewing) devices, etc., are then inserted through the one or more cannulas.

When considering what size cannula to use for a given procedure, surgeons often face a tradeoff. On the one hand, smaller cannulas can lead to better patient outcomes including less peri-operative pain, rapid return of normal functions, earlier return to home and work, and reduced herniation risk. On the other hand, smaller cannulas can reduce the selection of MIS instruments available to the surgeon. For example, while many MIS instruments may have a shaft diameter that will fit through a smaller cannula, such instruments are often limited only to having straight shafts. By contrast, larger cannulas also accommodate surgical instruments having bent shafts that require a larger diameter cannula tube for passage.

Surgical instruments having a bend are often more ergonomic, enabling a surgeon to work more comfortably, efficiently, and to reach areas inside the patient which would otherwise be very difficult to access with a straight-shafted MIS instrument. In light of these advantages, this can lead surgeons to use larger size cannulas to ensure a successful, efficient procedure at the possible expense of patient recovery time for the reasons discuss above.

In response to this situation, surgical instruments with articulation control have been developed. With these instruments, the surgeon is able to adjust a dial, knob, lever, or other control on the proximal end of the instrument to first straighten the shaft. In its straight profile, the shaft can easily be passed through a smaller diameter cannula tube. Once the distal end of the MIS instrument is inside the patient, the surgeon can then readjust the control on the proximal end to articulate the tip of the device into an operating position. When the instrument needs to be removed, the surgeon can further adjust the control on the proximal end to articulate the distal shaft of the device into a straight position so that it can be removed through the cannula. Unfortunately, while such controlled-articulation devices do allow surgeons to use smaller cannulas, they can complicate the surgical procedure by requiring two hands to operate the device, one to hold the proximal end of the device and another to adjust the articulation control. The surgeon may not have a free hand for the articulation control, since he or she may also be manipulating another device through a separate cannula at the same time with his or her other hand. As a result, a surgical assistant may be needed to help out in these situations, or the surgeon may temporarily have to let go of the other device, possibly leaving it momentarily unattended.

Therefore, there is a need for technology which 1) will enable a surgeon to use ergonomically bent or angled MIS instruments 2) in conjunction with smaller cannula sizes to improve patient outcomes and recovery times 3) while freeing the surgeon from the need to control articulation of the MIS instrument.

SUMMARY

A self-articulating joint is disclosed for a minimally invasive surgical apparatus. The self-articulating joint has a first elbow component pivotably coupled to a second elbow component, wherein the first and second elbow components are biased to form a non-linear angle relative to each other. The self-articulating joint also has an elbow latch configured to releasably hold the first and second elbow components at a substantially fixed non-linear operating angle.

A minimally invasive surgical apparatus is also disclosed. The minimally invasive surgical apparatus has a manipulation interface and a proximal shaft coupled to the manipulation interface at a first end of the proximal shaft. The minimally invasive surgical apparatus also has a surgical end effector configured to be controlled by the manipulation interface. The minimally invasive surgical apparatus further has a distal shaft coupled to the end effector at a first end of the distal shaft. The minimally invasive surgical apparatus also has at least one self-articulating joint coupled between a second end of the proximal shaft and a second end of the distal shaft.

Another self-articulating joint is disclosed for a surgical suturing apparatus. The self-articulating joint has a first elbow component and a second elbow component pivotably coupled to the first elbow component. The first elbow component has at least one functional channel and a latch catch. The second elbow component has 1) a joint biasing element configured to bias the first and second elbow components to form a non-linear angle relative to each other; and 2) at least one other functional channel corresponding to the at least one functional channel of the first elbow component. The self-articulating joint also has an elbow latch, held by the second elbow component, configured to engage the latch catch of the first elbow component to releasably hold the first and second elbow components at a substantially fixed non-linear operating angle. The elbow latch is moveable between i) a latched position where the first and second elbow components can be releasably held in the substantially fixed non-linear operating angle; and ii) an unlatched position where the first and second elbow components are released from being held in the substantially fixed non-linear operating angle. The elbow latch also includes a latch spring configured to bias the elbow latch towards the latched position. The elbow latch further includes a button configured to be engaged by a cannula surface which, when engaged, will cause the elbow latch to release the first and second elbow components from being held in the substantially fixed non-linear operating angle.

BRIEF DESCRIPTION OF THE DRAWINGS

FIGS. 4A-4F illustrate one embodiment of an MIS apparatus, having a self-articulating joint, passing from outside of a patient, through a cannula, and into the patient.

FIGS. 7A-7F illustrate another embodiment of an MIS apparatus, having a self-articulating joint, passing from outside of a patient, through a cannula, and into the patient.

FIGS. 8B-8D schematically illustrate activation of the elbow latch of the self-articulating joint of FIG. 8A and an ensuing articulation.

FIGS. 9-10 schematically illustrate other embodiments of a self-articulating joint having further examples of a joint biasing element.

Figure 1A:
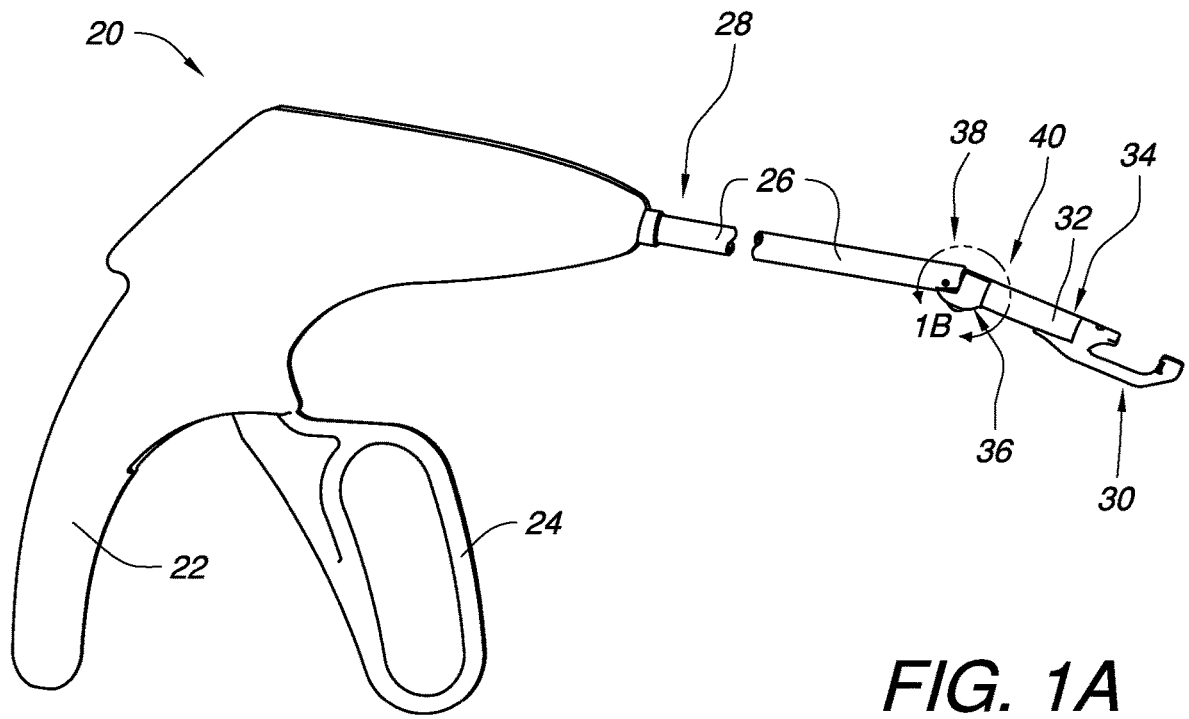
FIG. 1A is a perspective view of one embodiment of a minimally invasive surgical (MIS) apparatus having a self-articulating joint coupled between proximal and distal shafts.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1A schematically illustrates one embodiment of a minimally invasive surgical (MIS) apparatus 20. Generally speaking, an MIS apparatus can be configured to be manipulated directly in the hand of a surgeon or indirectly by coupling the MIS apparatus to a surgical robotic platform, such as the da Vinci® Surgical System. Whether the MIS apparatus is intended to be manipulated by hand or by machine interface, an MIS apparatus will have a manipulation interface, such as, but not limited to, the handle 22 with actuator 24 of the MIS apparatus 20 in FIG. 1. The MIS apparatus 20 also has a proximal shaft 26 coupled to the handle 22 at a first end 28 of the proximal shaft 26.

MIS apparatuses are also designed to have at least one surgical end effector configured to be controlled by the manipulation interface. Although the term "end effector" is sometimes used in the robotics field to refer to a device at the end of a robotic arm designed to interact with the environment, here, the term is used in a broader fashion. As used herein, the term "surgical end effector" refers to any device at the end of the MIS apparatus designed to interact with and/or observe the surgical environment and controlled by the manipulation interface, whether or not the MIS apparatus is being manipulated directly by a surgeon's hand or indirectly by robotic device. Some non-limiting examples of surgical end effectors may include suturing devices, endoscopic devices, imaging devices, gripping devices, and cutting devices.

In the example of FIG. 1A, the MIS apparatus 20 has a suturing surgical end effector 30 configured to be controlled by the manipulation interface (in this case, the handle 22 and the actuator 24). For convenience, many of the embodiments discussed herein are surgical suturing devices. The suturing technology will not be discussed at great length in this application, as suitable suturing methods are known to those skilled in the art which can readily be used with the novel and non-obvious self-articulating joint which is described and claimed herein. For example, U.S. Pat. No. 7,407,505 to Sauer, entitled "Running Stitch Suturing Device" provides suitable examples and is hereby incorporated by reference in its entirety.

The MIS apparatus of FIG. 1A also has a distal shaft 32 coupled to the end effector 30 at a first end 34 of the distal shaft 32. Although the distal shaft 32 and the end effector 30 are illustrated as separate parts in this embodiment, it should be understood that other embodiments may have the distal shaft 32 as a continuous part with the end effector 30.

Figure 1B:
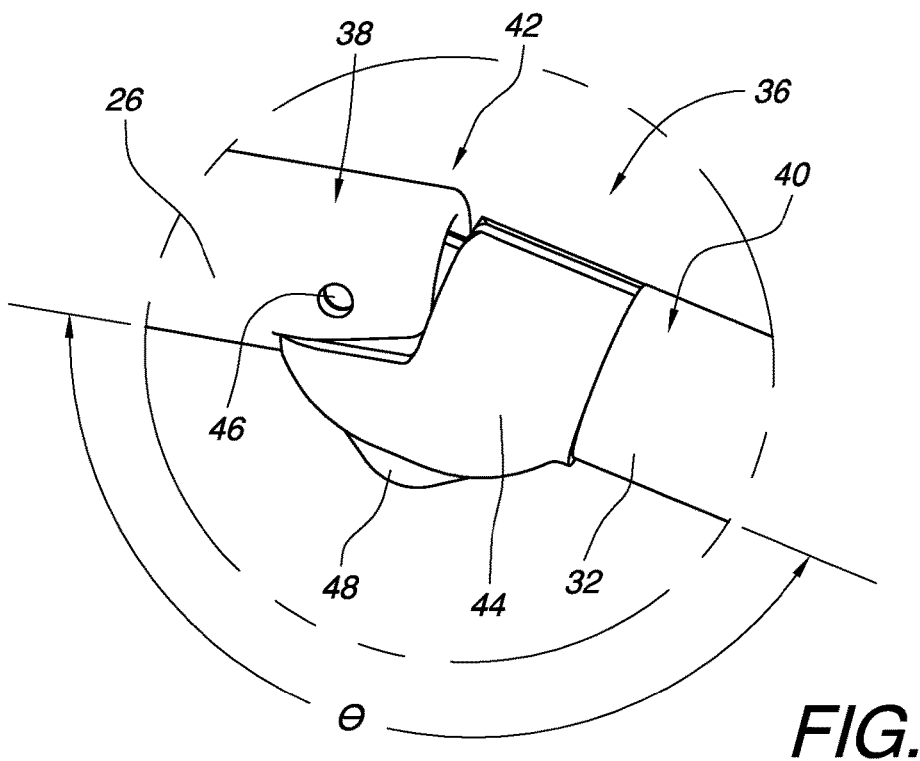
FIG. 1B shows an enlarged perspective view of the self-articulating joint of FIG. 1.

The MIS apparatus of FIG. 1A also has at least one self-articulating joint 36 coupled between a second end 38 of the proximal shaft 26 and a second end 40 of the distal shaft 32. FIG. 1B shows an enlarged perspective view of the self-articulating joint 36. The self-articulating joint 36 has a first elbow component 42 pivotably coupled to a second elbow component 44. In this embodiment, the first elbow component 42 is continuous with the proximal shaft 26, however, in other embodiments, the first elbow component 42 can be a separate part from, but coupled to, the proximal shaft 26. By contrast, in this embodiment, the second elbow component 44 is its own part separate from, but coupled to, the distal shaft 32. In other embodiments, the second elbow component 44 can be formed as a continuous part with the distal shaft 32.

In this embodiment, the first elbow component 42 is pivotably coupled to the second elbow component 44 by one or more pivot points 46. Those skilled in the art will understand that the first and second elbow components 42, 44 may be pivotably coupled in a variety of ways, including, but not limited to pivotable coupling by one or more flexible hinges, or pivotable coupling by a flexible material to which the first and second elbow components 42, 44 are both coupled. In some other embodiments, the first and second elbow components 42, 44 could be formed of a continuous material where at least a portion of the continuous material between the first and second elbow components comprises a flexible portion. In such an embodiment, the first elbow component could be coupled to the second elbow component by the continuous flexible portion.

In the self-articulating joint 36 embodiment of FIG. 1B, the first and second elbow components 42, 44 are biased, for example by a joint biasing element (not visible in this view) to form a non-linear angle relative to each other (as measured, for example, by comparison of the angle between the proximal and distal shafts 26, 32 to which the first and second elbow components 42, 44 are coupled or continuous with). Suitable non-limiting examples of a joint biasing element will be illustrated and discussed later in this specification.

A button 48 is also visible in the illustration of FIG. 1B. The button 48 is a part of an elbow latch (not visible in this view) which will be illustrated and discussed in more detail later in this specification. The elbow latch is configured to releasably hold the first and second elbow components at a substantially fixed non-linear operating angle θ. The elbow latch may include a button 48 configured to be engaged by a cannula surface (not shown in this view). The button 48, when engaged, causes the elbow latch to release the first and second elbow components 42, 44 from being held in the substantially fixed non-linear operating angle θ.

Figure 2A:
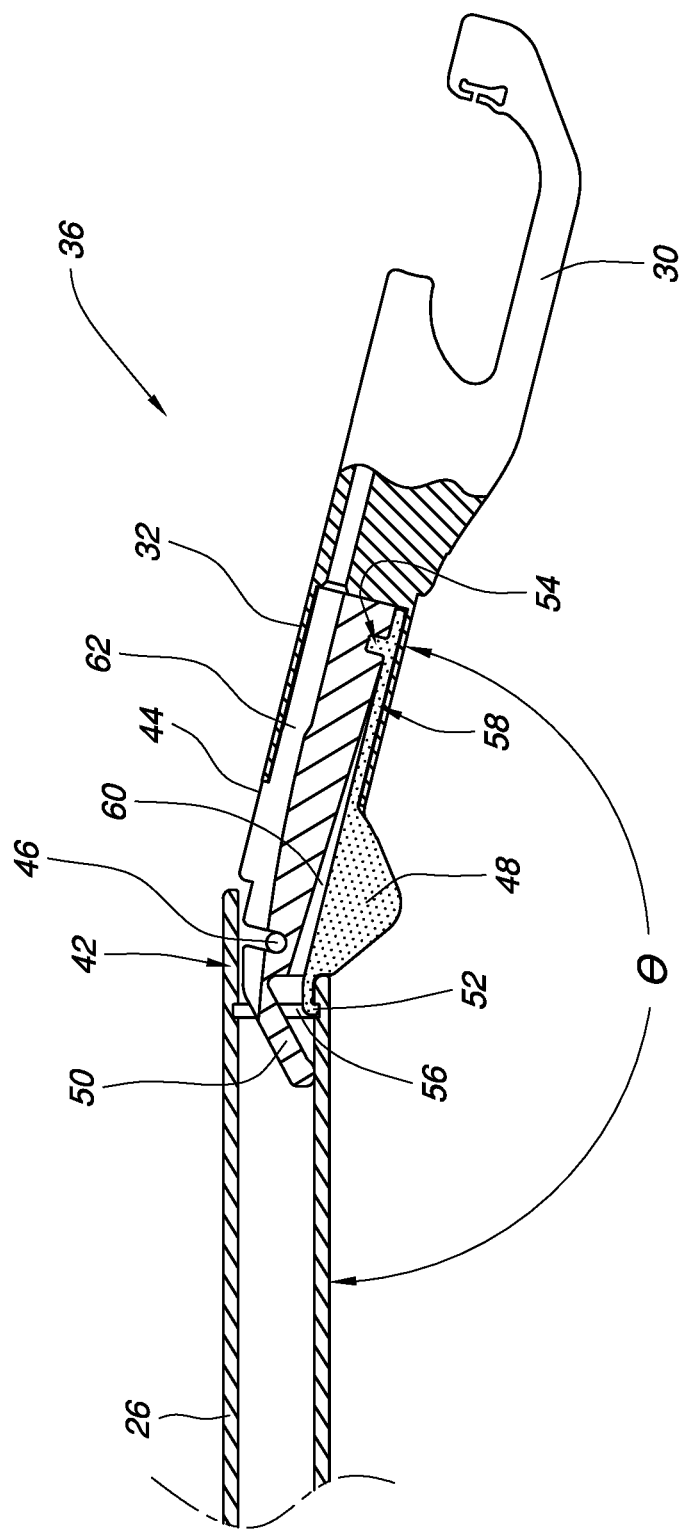
FIG. 2A is a partial cross-sectional view of a portion of an MIS apparatus having one embodiment of a self-articulating joint where the elbow latch is in a latched position.

FIG. 2A is an enlarged partial cross-sectional view of a portion of the MIS apparatus and self-articulating joint 36 of FIGS. 1A-1B. As discussed above, the first elbow component 42 is pivotably coupled to the second elbow component 44. The first and second elbow components 42, 44 are biased by joint biasing element 50 to form a non-linear angle relative to each other. In this embodiment, the joint biasing element 50 is a flexible leaf integral with the second elbow component 44. The joint biasing element 50 pushes against the inside of the proximal shaft 26 to bias the first and second elbow components 42, 44 towards a non-linear angle.

An elbow latch 52 can also be seen in in FIG. 2A. In this embodiment, the elbow latch 52 is located on the inside of the substantially fixed non-linear operating angle θ of the first and second elbow components. The elbow latch 52 is configured to releasably hold the first and second elbow components 42, 44 at the substantially fixed non-linear operating angle θ. In this embodiment, the second elbow component 44 is configured to hold the elbow latch 52, for example via keyed portion 54. The first elbow component 42 has a latch catch 56, in this case, a groove running inside at least a portion of the first elbow component 42. The latch catch 56 is configured to be engaged by the elbow latch 52 to releasably hold the first and second elbow components 42, 44 at the substantially fixed non-linear operating angle θ.

Figure 2B:
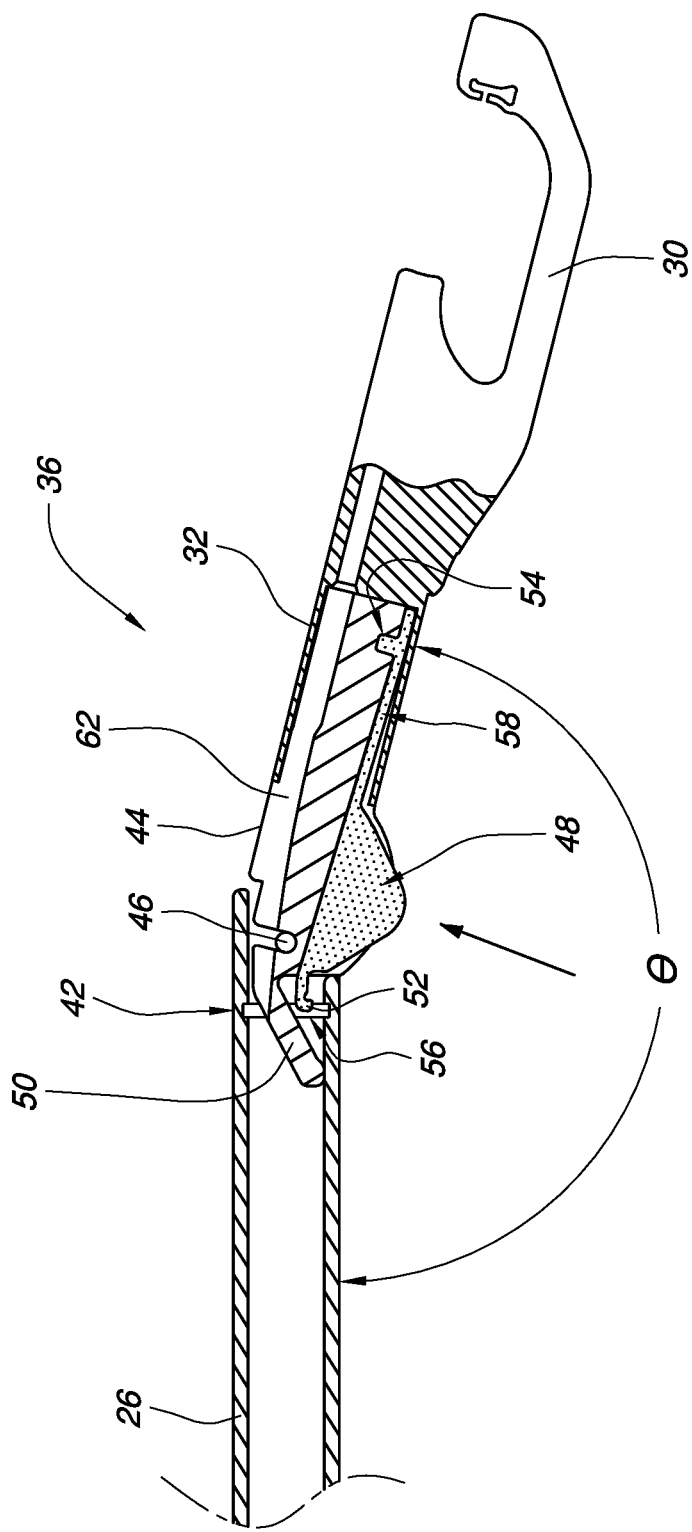
FIG. 2B is a partial cross-sectional view of the MIS apparatus of FIG. 2A where the elbow latch is in an unlatched position.

The elbow latch 52 is moveable between a latched position (as shown in FIG. 2A) and an unlatched position (as shown in FIG. 2B). In the embodiment of FIG. 2A, the elbow latch 52 also includes a latch spring 58 which allows the elbow latch 52 to be unlatched by pushing the button 48 to flex the latch spring 58 back into a void 60 in the elbow component 44. In other embodiments, the latch spring may be a separate component from the elbow latch 52. When the elbow latch 52 is unlatched, a force can be applied to the device to overcome the spring force of the joint biasing element 50 thereby allowing the angle between the proximal shaft 26 and the distal shaft 32 to be substantially straightened until the spring force of the joint biasing element 50 is allowed to take over, whereby the latched position of FIG. 2A can be reestablished if the button 48 is no longer engaged.

Depending on the type of surgical end effector 30 located at the distal end of the device, it may be desirable to enable the passage and/or movement of one or more guide wires, control cables, needles, fiber optics, electrical wires, lumens, suction tubes, and the like from the proximal shaft 26, through the self-articulating joint 36, and to the distal shaft 32. Accordingly, the first and/or second elbow components 42, 44 may include one or more functional channels 62 to accommodate such access between the proximal and distal shafts 26, 32.

Figure 3A:
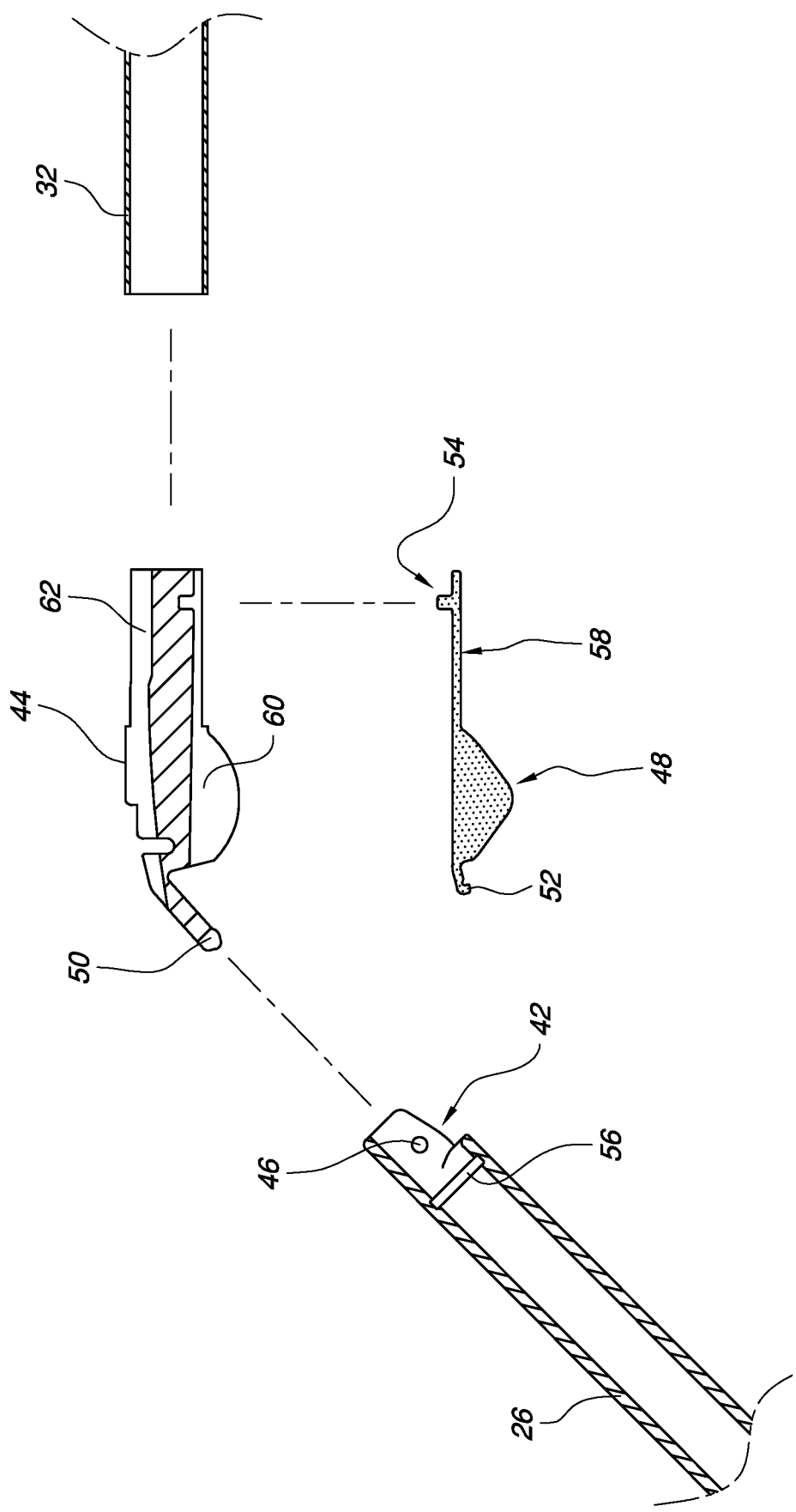
FIG. 3A is an exploded cross-sectional view of the self-articulating joint embodied in FIG. 2A.
Figure 3B:
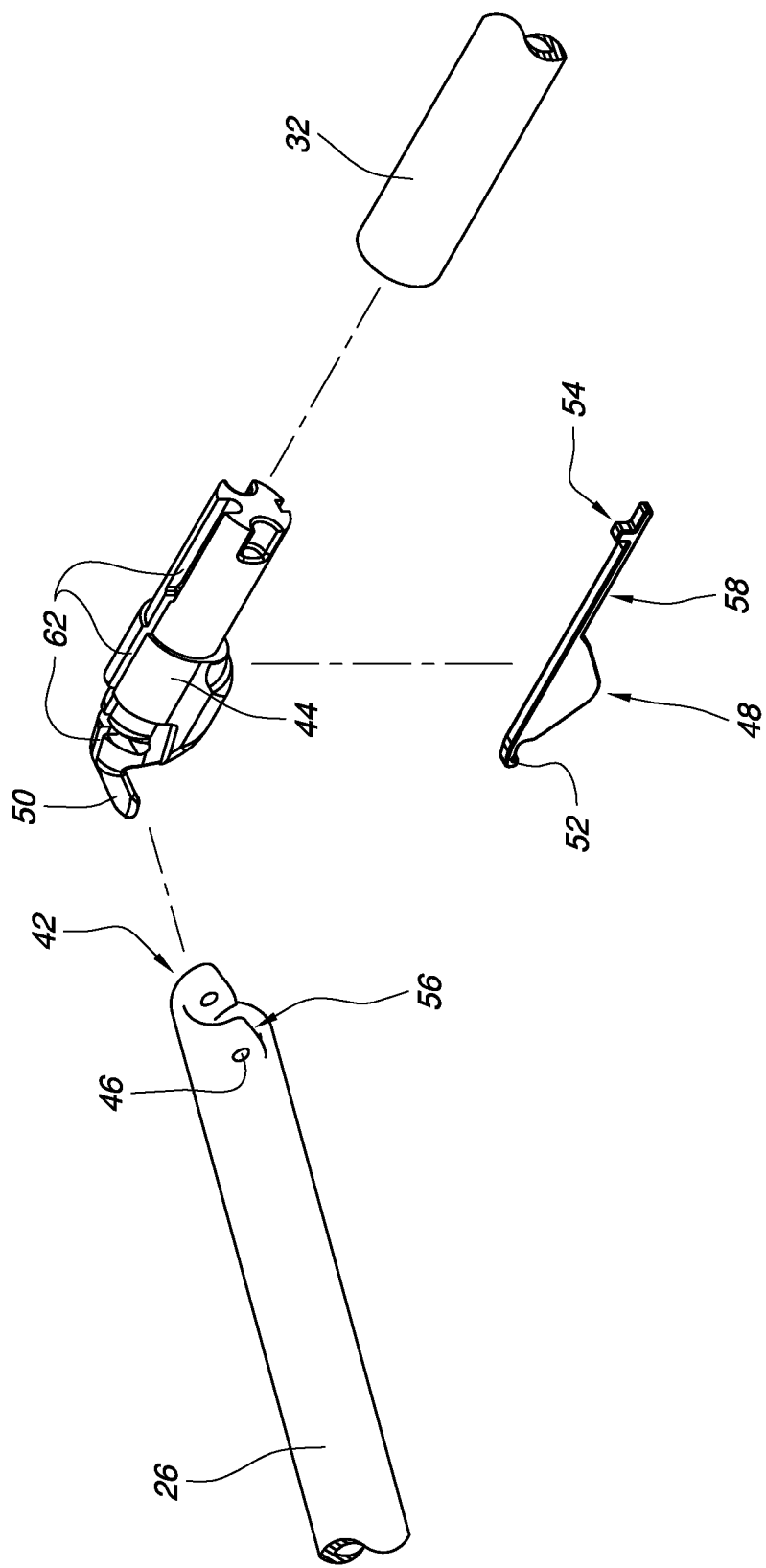
FIG. 3B is an exploded perspective view of the self-articulating joint embodied in FIG. 2A.

FIG. 3A is an exploded cross-sectional view of the self-articulating joint 36 embodied in FIG. 2A. Similarly, FIG. 3B is an exploded perspective view of the self-articulating joint 36 embodied in FIG. 2A. The exploded views of FIGS. 3A and 3B provide an opportunity to see the elements previously discussed from a different point of view.

Figure 4A:
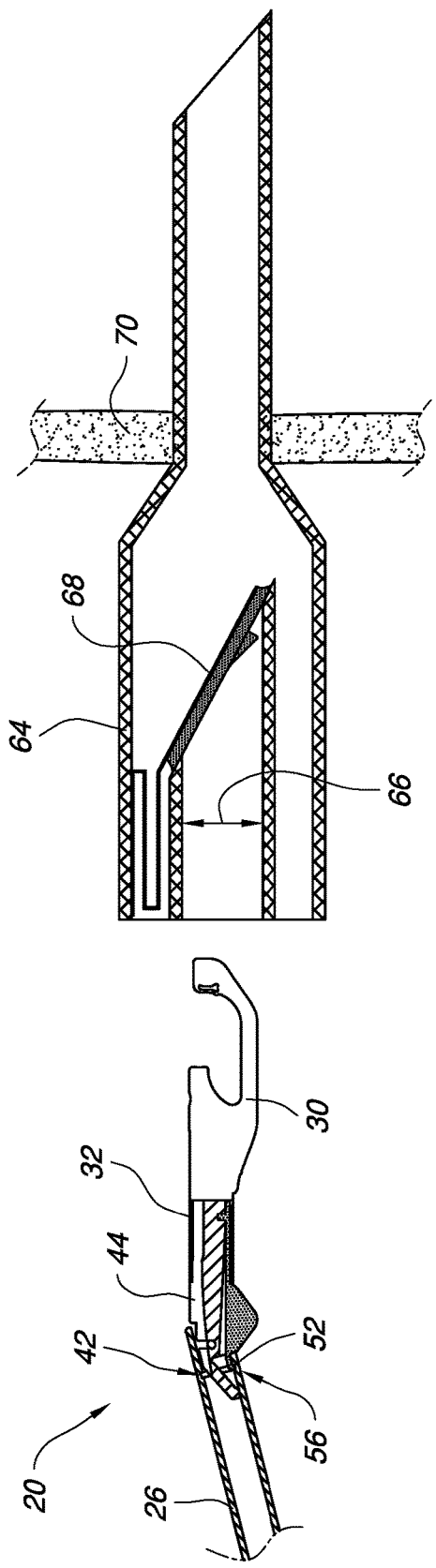
Figure 4B:
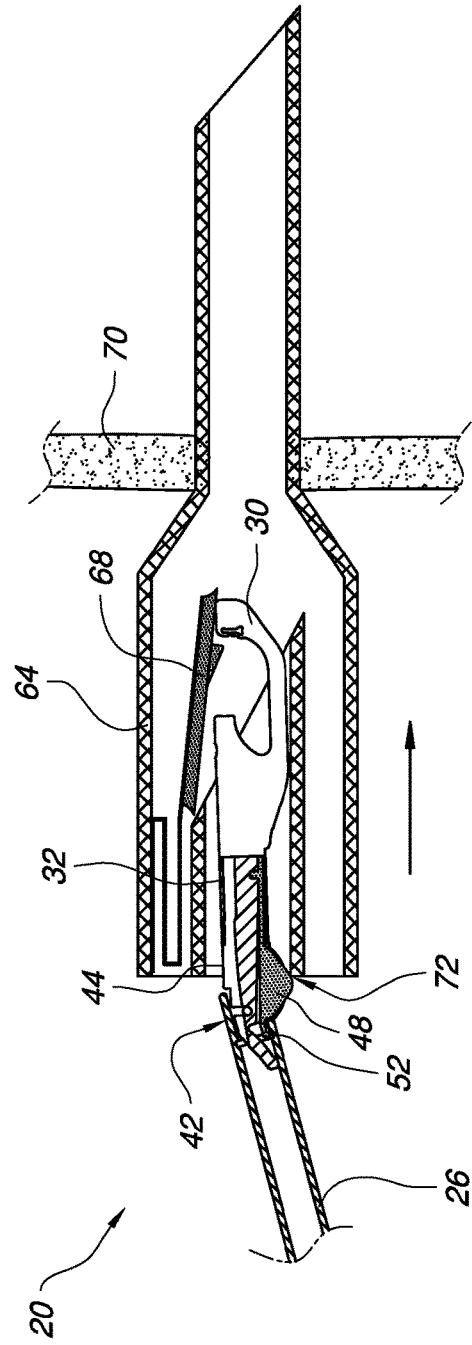

A self-articulating joint for a minimally invasive surgical apparatus is highly desirable because it can be used to automatically and temporarily align the proximal and distal shafts of a normally bent or angled surgical apparatus to enable passage of the functional end of the apparatus through a small diameter cannula while still enabling a bend or angle in the device to be reestablished once inside a body cavity. FIGS. 4A-4F illustrate one embodiment of an MIS apparatus 20, having a self-articulating joint, passing from outside of a patient, through a cannula 64, and into the patient. The cannula 64 has an inner diameter 66 and may be equipped with a sealing flap 68. The cannula 64 is used to maintain a convenient minimally invasive access point through a patient's tissue 70. As shown in FIG. 4A, the MIS apparatus 20 is entirely outside of the patient and has not yet entered the cannula 64. The elbow latch 52 is engaging the latch catch 56 and is in the latched position whereby the first and second elbow components 42, 44 are being held at a substantially fixed non-linear operating angle. As shown in FIG. 4B, the MIS apparatus 20 has been positioned so that the surgical end effector 30 and the distal shaft 32 have entered the cannula 64. It should be noted that without the self-articulating joint, an MIS apparatus 20 having this type of angle between the proximal and distal shafts 26, 32 would not fit through a cannula 64 having such a small inner diameter 66. In FIG. 4B, the elbow latch button 48 is just starting to contact a cannula opening surface 72. As discussed above, this will cause the elbow latch 52 to move from a latched position to an unlatched position, thereby releasing the first and second elbow components 42, 44 from being held in a substantially fixed non-linear operating angle.

With the elbow latch 52 in an unlatched position, the surgeon is free to pivot the proximal shaft 26 into substantial alignment with the distal shaft 32 while pushing the MIS apparatus 20 farther into the cannula 64 as illustrated in FIG. 4C. FIG. 4D simply illustrates the MIS apparatus 20 even farther into the cannula 64, with the surgical end effector 30 progressing into an exit portion 74 of the cannula 64.

As illustrated in FIG. 4E, the cannula 64 may have a middle region 76 outside of the patient which is larger than the inner diameter 66 in the entrance portion 78 or in the exit portion 74 of the cannula 64. Depending on the particular embodiment, this extra space may provide an opportunity for the self-articulating joint 36 to bias itself back into a fixed non-linear operating angle where the elbow latch 52 moves back into the latched position while the elbow joint 36 is still in the cannula 64. If this were to happen, however, the button 48 can be engaged by any inner surface 80, thereby unlatching the elbow latch 52 again.

As the MIS apparatus 20 continues to be advanced through the cannula 64, the distal shaft 32 and the self-articulating joint 36 will eventually exit the cannula 64 inside the patient as shown in FIG. 4F. The joint biasing element 50 will push the distal shaft 32 into a non-linear angle with respect to the proximal shaft 26 until the elbow latch 52 re-engages with the latch catch 56, holding the first and second elbow components 42, 44 at the substantially fixed non-linear operating angle.

Figure 4G:
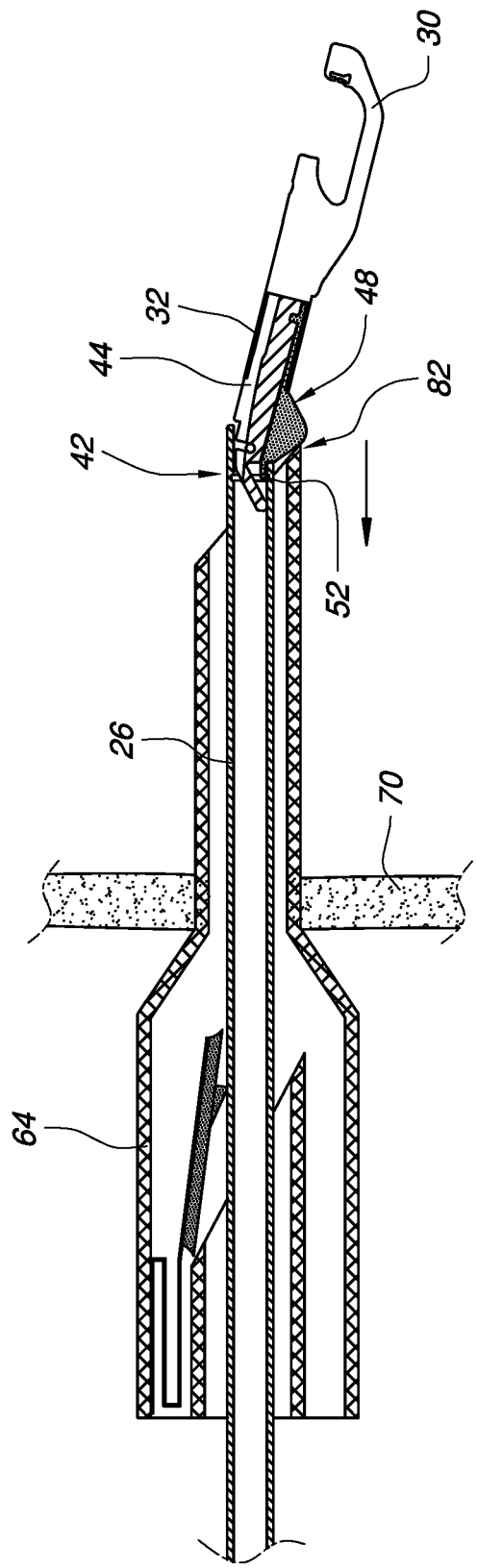
FIG. 4G illustrates the MIS apparatus of FIGS. 4A-4F just before the self-articulating joint passes back through the cannula while the MIS apparatus is being removed from the patient.

A surgeon may manipulate the MIS apparatus 20 as desired, taking advantage of the bent configuration inside the patient's body while the patient can enjoy an improved outcome and reduced recovery time by virtue of the small cannula being used. When it is time to remove the MIS apparatus 20 from the patient, the device is withdrawn as illustrated in FIG. 4G. The button 48 will come into contact with a cannula exit surface 82. As discussed above, this will cause the elbow latch 52 to move from a latched position to an unlatched position, thereby releasing the first and second elbow components 42, 44 from being held in a substantially fixed non-linear operating angle. With the elbow latch 52 in an unlatched position, the distal shaft 32 is free to pivot into substantial alignment with the proximal shaft 26 and thereafter be drawn out of the patient via the cannula 64.

Figure 5A:
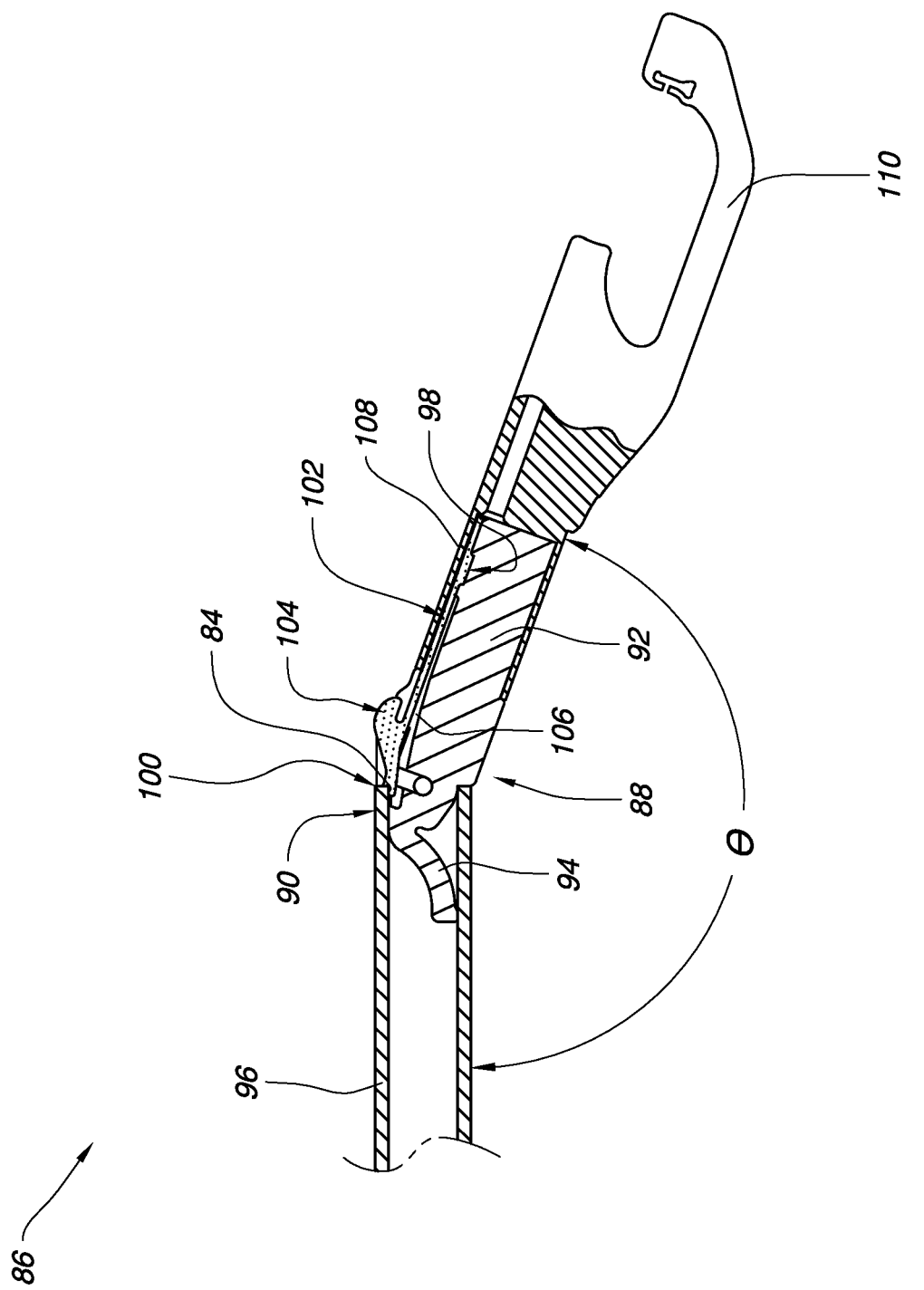
FIG. 5A is a partial cross-sectional view of a portion of an MIS apparatus having another embodiment of a self-articulating joint where the elbow latch is in a latched position.

Thus far, the illustrated embodiments have included an elbow latch which is located on the inside of the elbow. As another non-limiting example, the embodiment of FIG. 5A has an elbow latch 84 which is located on the outside of the elbow. FIG. 5A is an enlarged partial cross-sectional view of a portion of an MIS apparatus 86 and self-articulating joint 88. The self-articulating joint 88 has a first elbow component 90 that is pivotably coupled to a second elbow component 92. The first and second elbow components 90, 92 are biased by joint biasing element 94 to form a non-linear angle relative to each other. In this embodiment, the joint biasing element 94 is a flexible leaf integral with the second elbow component 92. The joint biasing element 94 pushes against the inside of the proximal shaft 96 to bias the first and second elbow components 90, 92 towards a non-linear angle.

In the embodiment of FIG. 5A, the elbow latch 84 is located on the outside of the substantially fixed non-linear operating angle θ of the first and second elbow components 90, 92. The elbow latch 84 is configured to releasably hold the first and second elbow components 90, 92 at the substantially fixed non-linear operating angle θ. In this embodiment, the second elbow component 92 is configured to hold the elbow latch 84, for example via keyed portion 98. The first elbow component 90 does not have a grooved latch catch like previous embodiments. Instead, the first elbow component's outer edge 100 serves as a latch catch which is configured to be engaged by the elbow latch 84 to releasably hold the first and second elbow components 90, 92 at the substantially fixed non-linear operating angle θ.

Figure 5B:
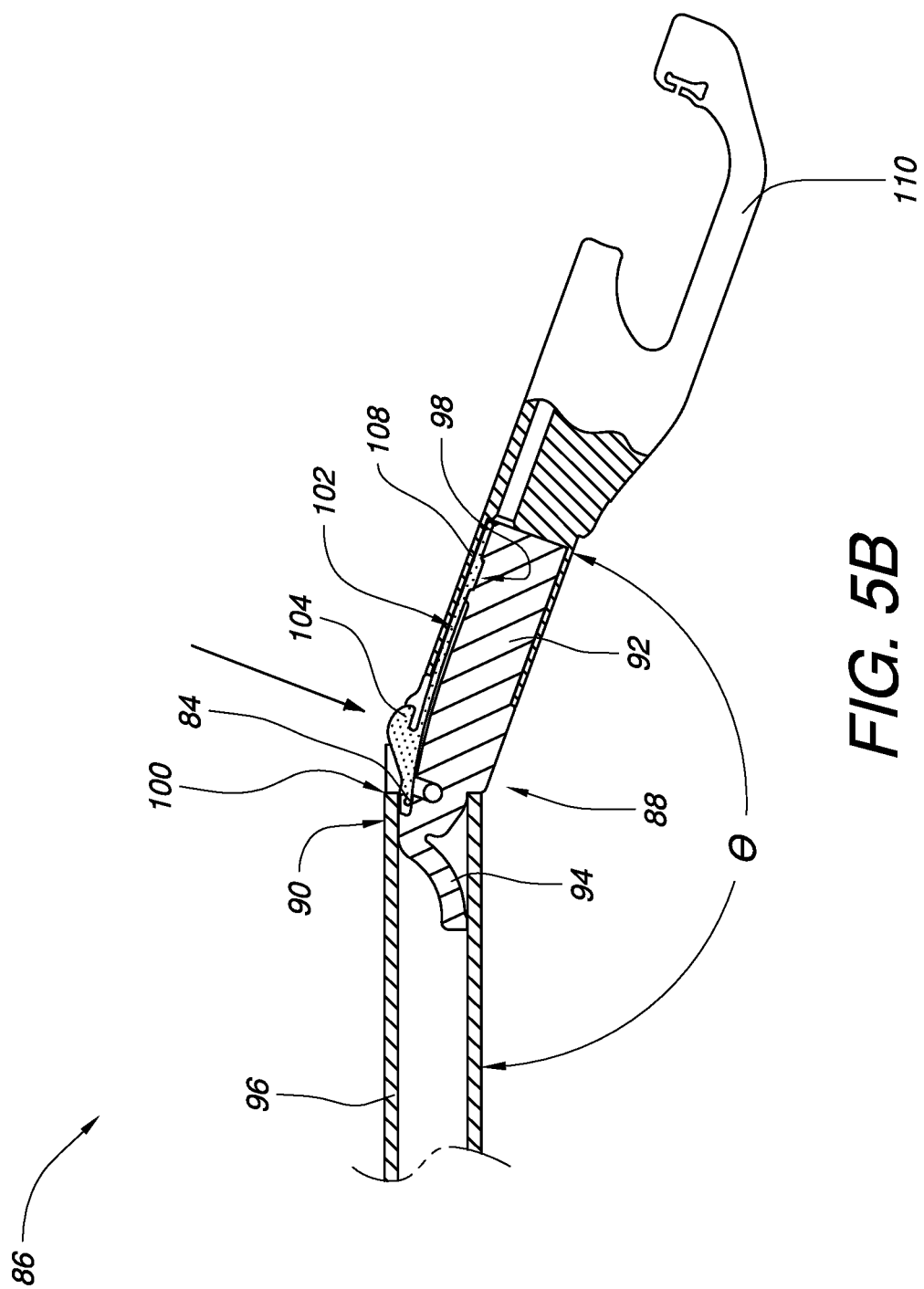
FIG. 5B is a partial cross-sectional view of the MIS apparatus of FIG. 5A where the elbow latch is in an unlatched position.

The elbow latch 84 is moveable between a latched position (as shown in FIG. 5A) and an unlatched position (as shown in FIG. 5B). In the embodiment of FIG. 5A, the elbow latch 84 also includes a latch spring 102 which allows the elbow latch 84 to be unlatched by pushing the button 104 to flex the latch spring 102 back into a void 106 in the elbow component 92. In other embodiments, the latch spring may be a separate component from the elbow latch 84. When the elbow latch 84 is unlatched, a force can be applied to the device to overcome the spring force of the joint biasing element 94 thereby allowing the angle between the proximal shaft 96 and the distal shaft 108 to be substantially straightened until the spring force of the joint biasing element 94 is allowed to take over, whereby the latched position can be reestablished if the button 104 is no longer engaged.

The embodiment of FIG. 5A does not include any functional channels. However, depending on the type of surgical end effector 110 located at the distal end of the device, it may be desirable to enable the passage and/or movement of one or more guide wires, control cables, needles, fiber optics, electrical wires, lumens, suction tubes, and the like from the proximal shaft 96, through the self-articulating joint 88, and to the distal shaft 108. Accordingly, in such other embodiments, the first and/or second elbow components may include one or more functional channels as discussed previously.

Figure 6A:
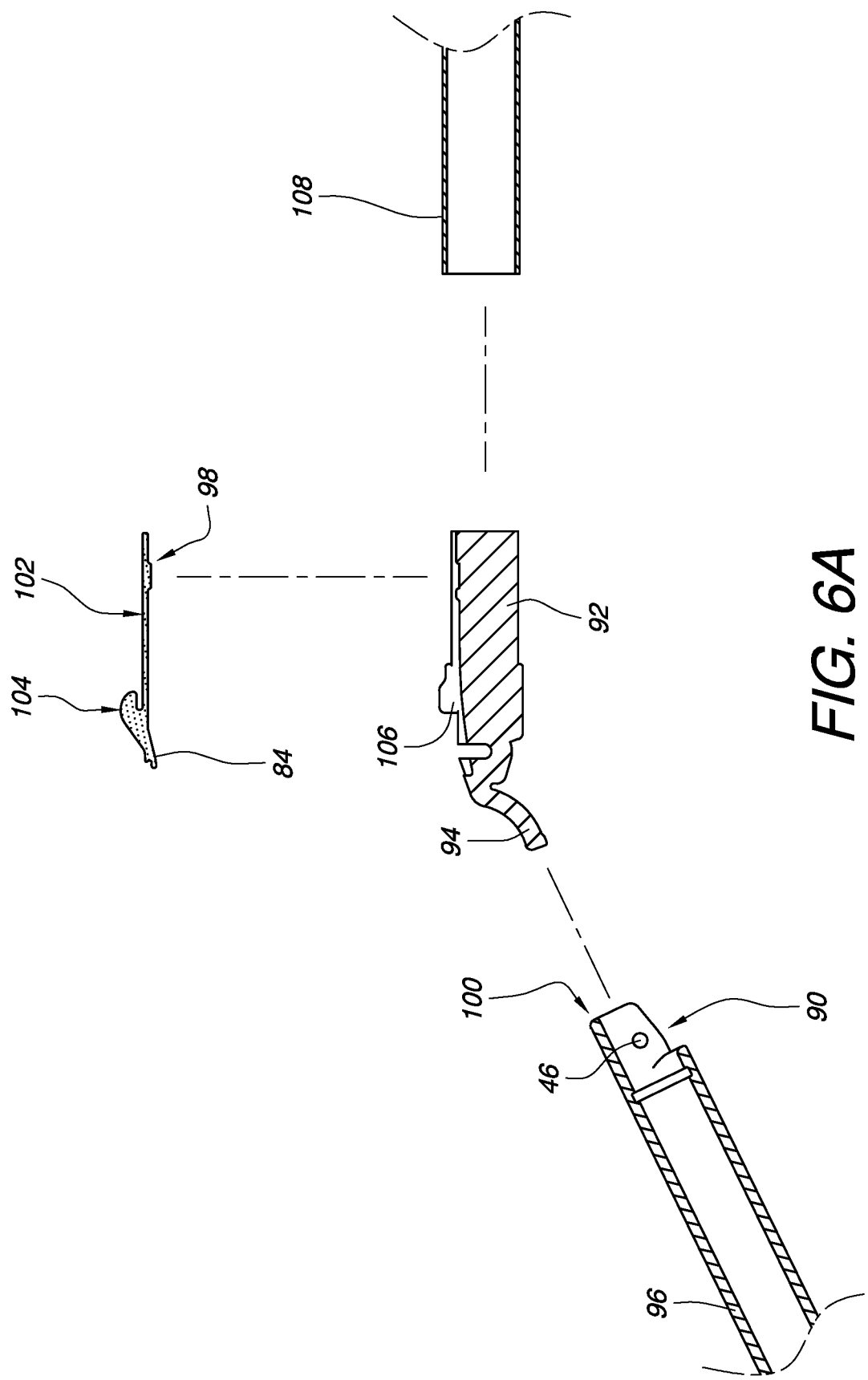
FIG. 6A is an exploded cross-sectional view of the self-articulating joint embodied in FIG. 5A.
Figure 6B:
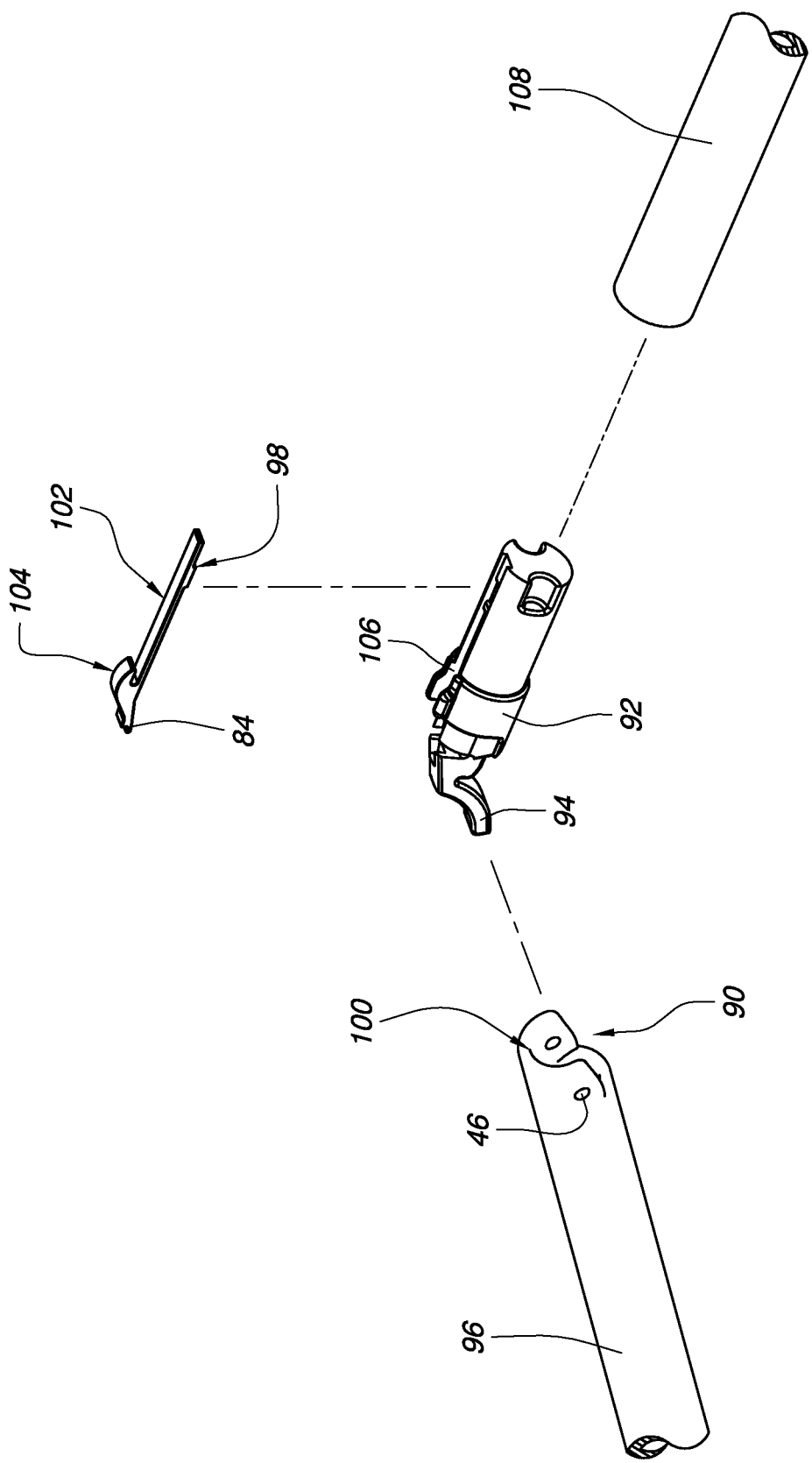
FIG. 6B is an exploded perspective view of the self-articulating joint embodied in FIG. 5A.

FIG. 6A is an exploded cross-sectional view of the self-articulating joint 88 embodied in FIG. 5A. Similarly, FIG. 6B is an exploded perspective view of the self-articulating joint 88 embodied in FIG. 5A. The exploded views of FIGS. 6A and 6B provide an opportunity to see the elements previously discussed from a different point of view.

As mentioned previously, the self-articulating joint for a minimally invasive surgical apparatus is highly desirable because it can be used to automatically and temporarily align the proximal and distal shafts of a normally bent or angled surgical apparatus to enable passage of the functional end of the apparatus through a small diameter cannula while still enabling a bend or angle in the device to be reestablished once inside a body cavity. FIGS. 7A-7F illustrate one embodiment of an MIS apparatus 86, having a self-articulating joint, passing from outside of a patient, through a cannula 64, and into the patient. As before, the cannula 64 has an inner diameter 66 and may be equipped with a sealing flap 68. The cannula 64 is used to make a convenient minimally invasive access point through a patient's tissue 70. As shown in FIG. 7A, the MIS apparatus 86 is entirely outside of the patient and has not yet entered the cannula 64. The elbow latch 84 is engaging the outer edge 100 of the first elbow component 90 and is in the latched position whereby the first and second elbow components 90, 92 are being held at a substantially fixed non-linear operating angle. As shown in FIG. 7B, the MIS apparatus 86 has been positioned so that the surgical end effector 110 and the distal shaft 108 have entered the cannula 64. It should be noted that without the self-articulating joint, an MIS apparatus 86 having this type of angle between the proximal and distal shafts 96, 108 would not fit through a cannula 64 having such a small inner diameter 66. In FIG. 7B, the elbow latch button 104 is just starting to contact a cannula opening surface 72. As discussed above, this will cause the elbow latch 84 to move from a latched position to an unlatched position, thereby releasing the first and second elbow components 90, 92 from being held in a substantially fixed non-linear operating angle.

With the elbow latch 84 in an unlatched position, the surgeon is free to pivot the proximal shaft 96 into substantial alignment with the distal shaft 108 while pushing the MIS apparatus 86 farther into the cannula 64 as illustrated in FIG. 7C. FIG. 7D simply illustrates the MIS apparatus 86 even farther into the cannula 64, with the surgical end effector 110 progressing into an exit portion 74 of the cannula 64.

As illustrated in FIG. 7E, the cannula 64 may have a middle region 76 outside of the patient which is larger than the inner diameter 66 in the entrance portion 78 or in the exit portion 74 of the cannula 64. Depending on the particular embodiment, this extra space may provide an opportunity for the self-articulating joint to bias itself back into a fixed non-linear operating angle where the elbow latch 84 moves back into the latched position while the joint is still in the cannula 64. If this were to happen, however, the button 104 can be engaged by any inner surface 80, thereby unlatching the elbow latch 84 again.

As the MIS apparatus 86 continues to be advanced through the cannula 64, the distal shaft 108 and the self-articulating joint 88 will eventually exit the cannula 64 inside the patient as shown in FIG. 7F. The joint biasing element 94 will push the distal shaft 108 into a non-linear angle with respect to the proximal shaft 96 until the elbow latch 84 re-engages with the outer edge 100, of the first elbow component 90, holding the first and second elbow components 90, 92 at the substantially fixed non-linear operating angle.

Figure 7G:
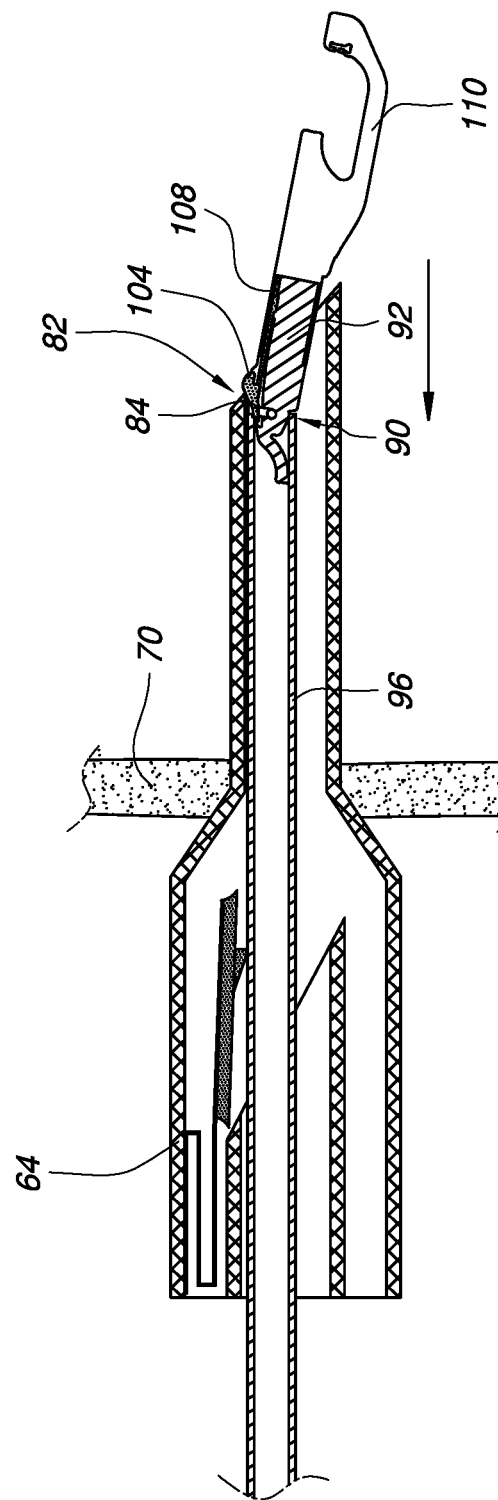
FIG. 7G illustrates the MIS apparatus of FIGS. 7A-7F just before the self-articulating joint passes back through the cannula while the MIS apparatus is being removed from the patient.

A surgeon may manipulate the MIS apparatus 86 as desired, taking advantage of the bent configuration inside the patient's body while the patient can enjoy an improved outcome and reduced recovery time by virtue of the small cannula being used. When it is time to remove the MIS apparatus 86 from the patient, the device is withdrawn as illustrated in FIG. 7G. The button 104 will come into contact with a cannula exit surface 82. As discussed above, this will cause the elbow latch 84 to move from a latched position to an unlatched position, thereby releasing the first and second elbow components 90, 92 from being held in a substantially fixed non-linear operating angle. With the elbow latch 84 in an unlatched position, the distal shaft 108 is free to pivot into substantial alignment with the proximal shaft 96 and thereafter be drawn out of the patient via the cannula 64.

Figure 8A:
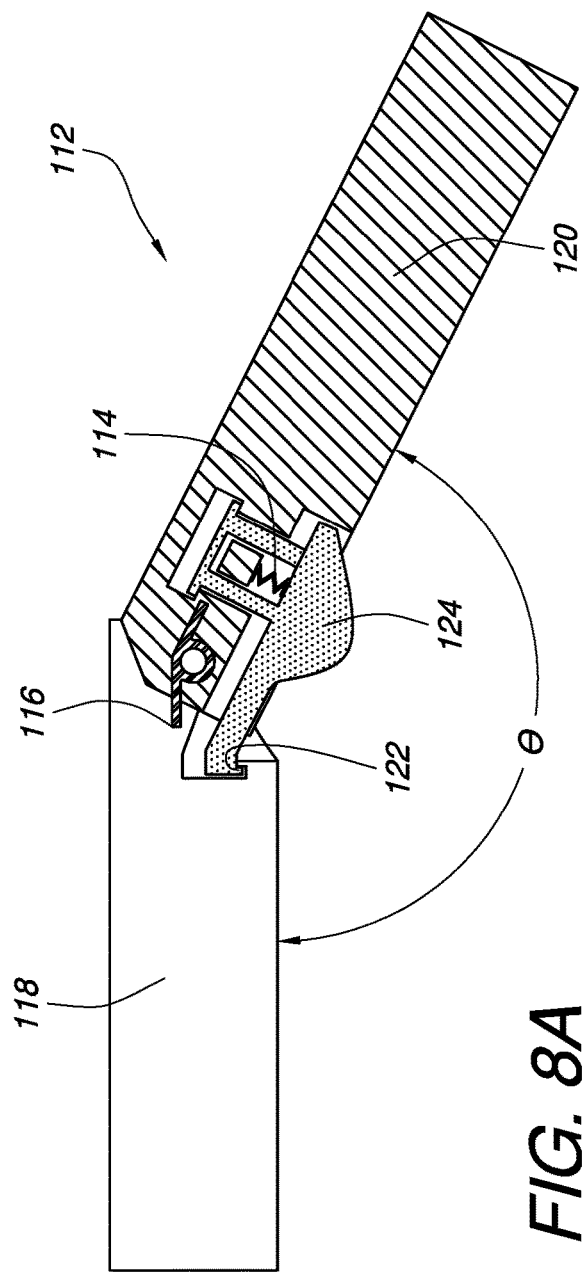
FIG. 8A schematically illustrates one embodiment of a self-articulating joint having other examples of a latch spring and a joint biasing element.

FIG. 8A schematically illustrates another embodiment of a self-articulating joint 112 having other examples of a latch spring 114 and a joint biasing element 116. Similar to the embodiments discussed above, the self-articulating joint 112 has a first elbow component 118 pivotably coupled to a second elbow component 120. The first and second elbow components 118, 120 are biased by the joint biasing element 116 to form a non-linear angle relative to each other. In this embodiment, the joint biasing element 116 is a coiled torsion spring.

Figure 8B:
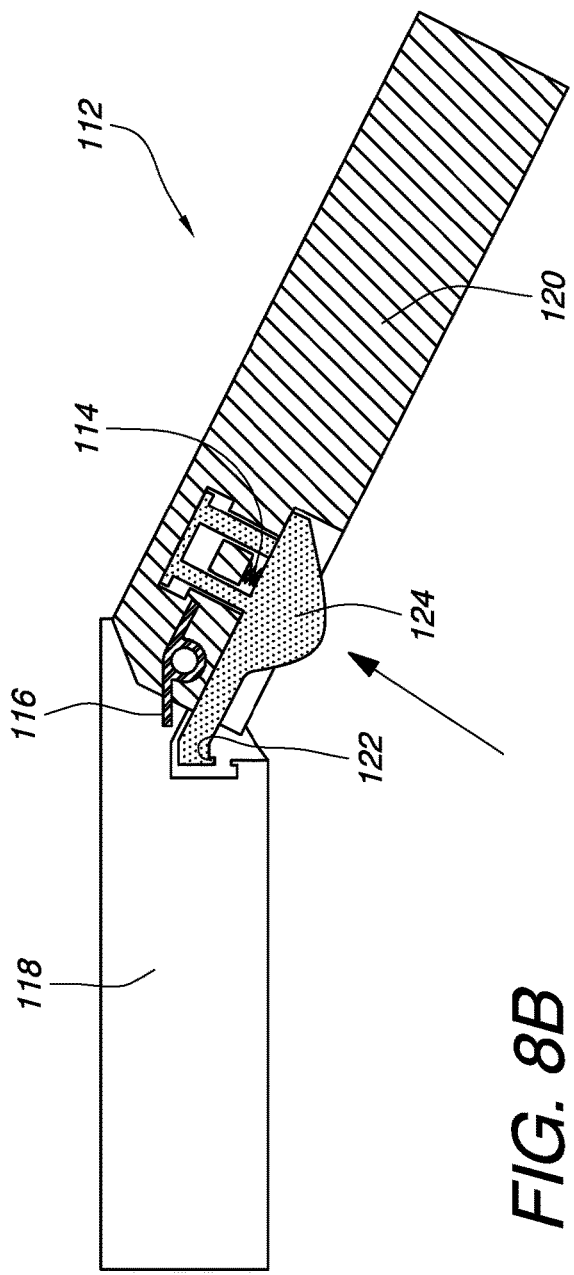

The self-articulating joint 112 also has an elbow latch 122 configured to releasably hold the first and second elbow components 118, 120 at a substantially fixed non-linear operating angle θ. As illustrated in FIG. 8A, the elbow latch 122 is in a latched position. However, the elbow latch 122 is also moveable between the latched position of FIG. 8A and the unlatched position illustrated in FIG. 8B. The latch spring 114, which is a separate component from the elbow latch 122 in this embodiment, is configured to bias the elbow latch 122 towards the latched position, so an external force must be applied to the elbow latch 122 in order to overcome the latch spring 114, thereby allowing the elbow latch 122 to move to the unlatched position. As with previous embodiments, the elbow latch 122 has a button 124 configured to be engaged by a cannula surface in order to unlatch the elbow latch 122 in FIG. 8A.

Once the self-articulating joint 112 is unlatched, it may be pivoted into other angles, including, but not limited to a substantially linear or straight angle as illustrated in FIGS. 8C and 8D. When external forces are removed, however, the joint biasing element 116 will reestablish the substantially fixed non-linear operating angle θ as held by the elbow latch 122.

FIGS. 9 and 10 schematically illustrate other embodiments of self-articulating joints 126, 128, respectively, having further examples of a joint biasing element. In FIG. 9, the self-articulating joint 126 is similar to the embodiment of FIG. 8A, however the embodiment of FIG. 9 has a leaf spring 130 as a joint biasing element. Some of the previous embodiments featured a leaf type spring, however, the leaf spring was integral with one of the elbow components. In this embodiment, the leaf spring 130 is a separate joint biasing element.

The embodiment of FIG. 10 is also similar to the embodiment of FIG. 8A, however, in the embodiment of FIG. 10, the joint biasing element 132 (shown schematically in cross-section) is a sleeve spring, for example, made from an elastic material which is wrapped around the self-articulating joint 128 and pre-formed to bias the first and second elbow components 118, 120 to form a non-linear angle relative to each other. Such a sleeve spring 132 could have an access slot or hole to allow button 124 to extend therethrough. In other embodiments, the sleeve spring 132 could completely cover the button 124 and elbow latch 122, thereby sealing the self-articulating joint 128. Other than having different joint biasing elements 130, 132, the embodiments of FIGS. 9 and 10 operate in a similar fashion to previously described embodiments.

Figure 11A:
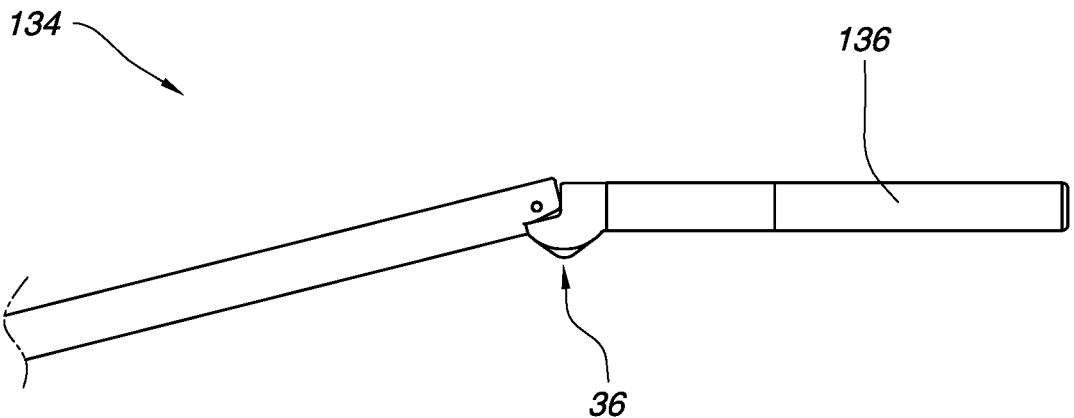
FIGS. 11A-11C schematically illustrate different embodiments of MIS apparatuses having a self-articulating joint.
Figure 11B:
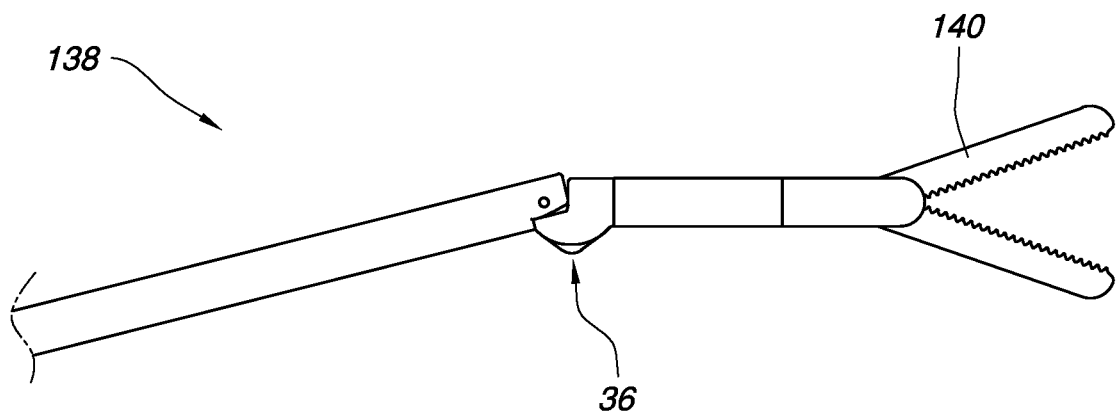
Figure 11C:
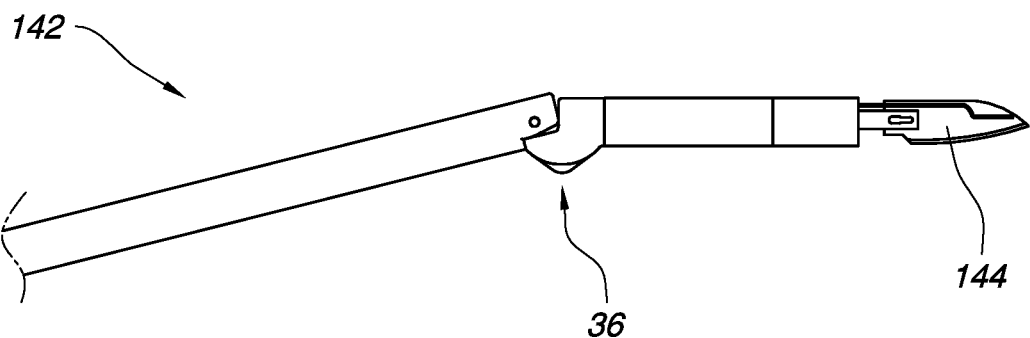

As mentioned previously, the surgical end effector of a minimally invasive surgical apparatus having a self-articulating joint could take on a variety of forms. For convenience, a suturing end effector has been illustrated in the embodiments thus far. FIGS. 11A-11C schematically illustrate different embodiments of MIS apparatuses having a self-articulating joint 36, the features of which have been discussed above. In FIG. 11A, the MIS apparatus 134 has an endoscopic end-effector 136. In FIG. 11B, the MIS apparatus 138 has a gripping end effector 140. In FIG. 11C, the MIS apparatus 142 has a cutting end effector 144. Those skilled in the art will appreciate that the self-articulating joints disclosed and claimed herein, as well as their equivalents, are readily usable with a wide variety of other types of end effectors.

Figure 12A:
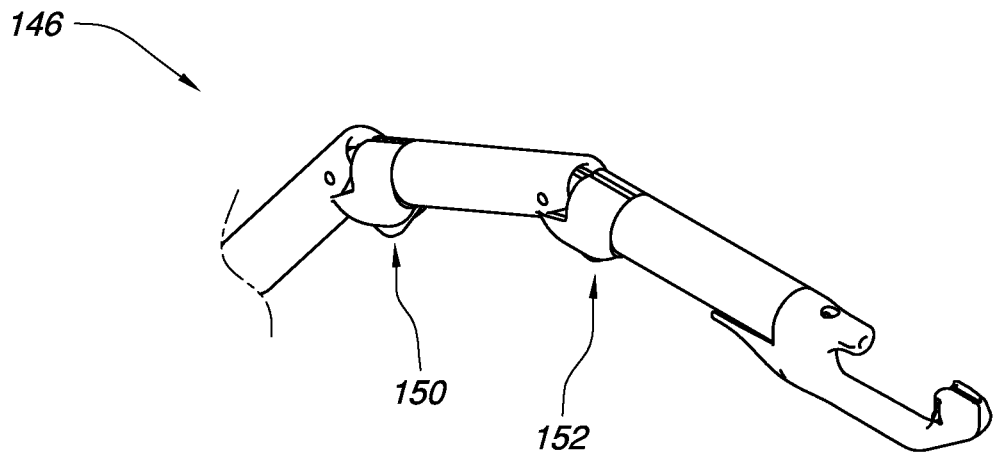
FIGS. 12A-12B are perspective views of MIS embodiments having multiple self-articulating joints.
Figure 12B:
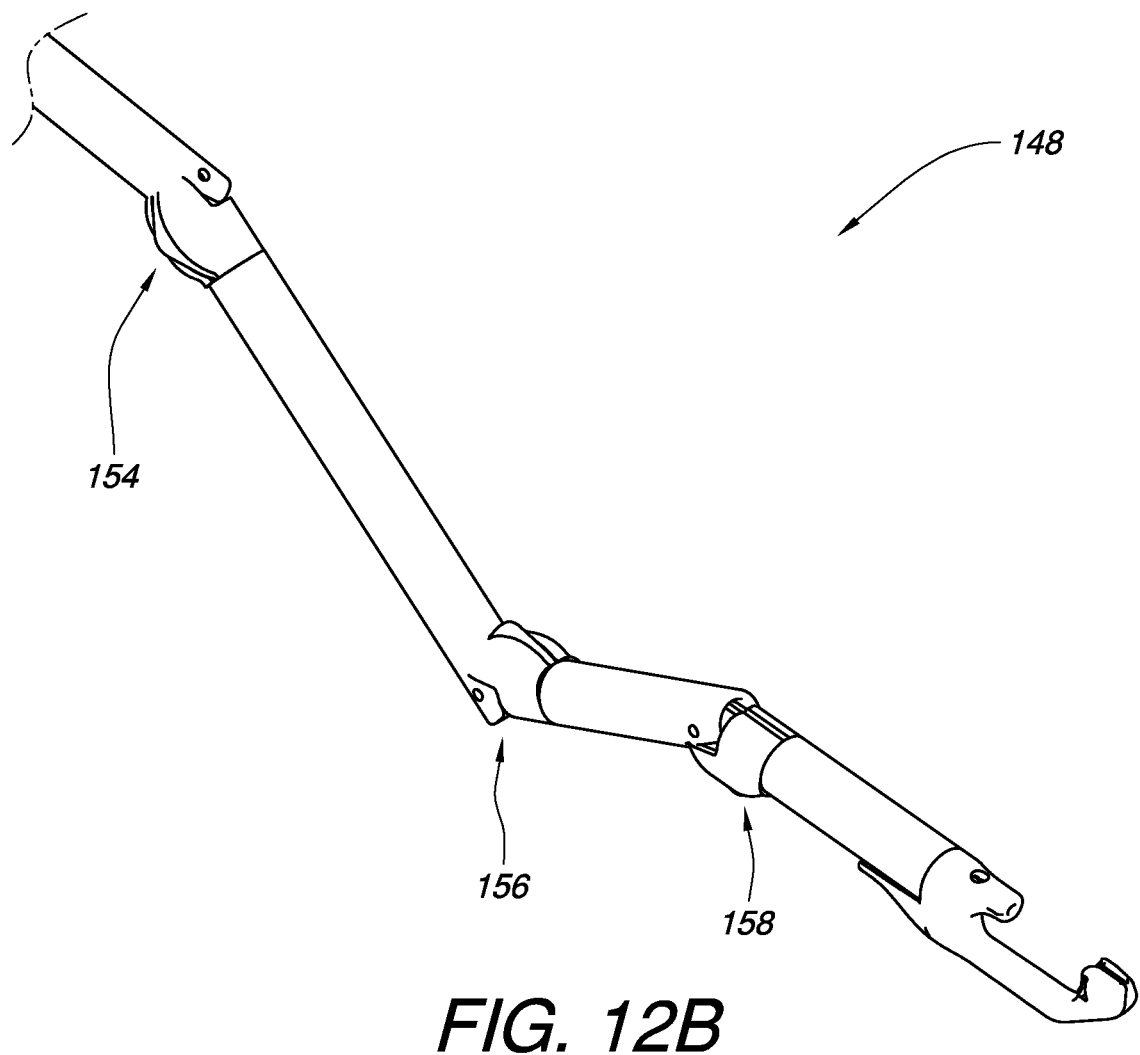

Thus far, the embodiments disclosed herein have included only a single self-articulating joint. However, embodiments having two or more self-articulating joints in a single MIS apparatus are possible. Each joint in such embodiments would operate similar to the single self-articulating joint examples discussed above. The only difference would be that the multiple self-articulating joints would be in the same apparatus. The button for each joint would be engageable by a cannula edge, thereby allowing devices with multiple bends to be inserted into and through a cannula as though they were just straight devices, while allowing the angled joints to be reestablished automatically after passing through. As just two examples, FIGS. 12A-12B are perspective views of MIS apparatus embodiments 146, 148, respectively. The embodiment of FIG. 12A has multiple self-articulating joints 150, 152 which pivot in the same plane for this example. The embodiment of FIG. 12B has multiple self-articulating joints 154, 156, 158 where self-articulating joint 154 pivots in a different plane from at least one of the other self-articulating joints 156, 158.

The ability 1) to add multiple self-articulating joints, 2) to choose the plane in which the self-articulating joints pivot, and 3) to vary the lengths of the shafts proximal and distal to each self-articulating joint provides enhanced freedom of design for MIS apparatus manufacturers, enabling MIS apparatuses with improved ergonomics and customizable reach profiles for hard to reach areas while still allowing surgeons to operate through minimally invasive openings.

Various advantages of a self-articulating joint for a minimally invasive surgical apparatus have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A minimally invasive surgical apparatus, comprising:
   a manipulation interface;
   a proximal shaft coupled to the manipulation interface at a first end of the proximal shaft;
   a surgical end effector configured to be controlled by the manipulation interface;
   a distal shaft coupled to the end effector at a first end of the distal shaft;
   at least one self-articulating joint coupled between a second end of the proximal shaft and a second end of the distal shaft;
   a first elbow component pivotably coupled to a second elbow component, wherein the first and second elbow components are biased to form a non-linear angle relative to each other; and
   an elbow latch configured to releasably hold the first and second elbow components at a substantially fixed non-linear operating angle.

2. The minimally invasive surgical apparatus of claim 1, wherein the manipulation interface is selected from the group consisting of a hand grip, a hand grip with a needle actuating lever, a hand grip with a gripper actuator; a handle; and a robotic interface.

3. The minimally invasive surgical apparatus of claim 1, wherein the surgical end effector is selected from the group consisting of a suturing apparatus, an endoscope apparatus, an imaging apparatus, a gripping apparatus, and a cutting apparatus.

4. The minimally invasive surgical apparatus of claim 1, wherein:
   the proximal shaft comprises one of the first and second elbow components; and/or
   the distal shaft comprises the other of the first and second elbow components.

5. The minimally invasive surgical apparatus of claim 1, wherein the surgical end effector comprises the distal shaft.

* * * * *